United States Patent
Downing et al.

(10) Patent No.: US 11,952,377 B2
(45) Date of Patent: Apr. 9, 2024

(54) QUINOLINES AND AZAQUINOLINES AS INHIBITORS OF CD38

(71) Applicant: BOEHRINGER INGELHEIM INTERNATIONAL GMBH, Ingelheim (DE)

(72) Inventors: Jennifer Downing, Cambridge, MA (US); Kevin Wayne Kuntz, Cambridge, MA (US); Laurie B. Schenkel, Cambridge, MA (US); Melissa Marie Vasbinder, Cambridge, MA (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 17/586,939

(22) Filed: Jan. 28, 2022

(65) Prior Publication Data
US 2022/0242862 A1    Aug. 4, 2022

Related U.S. Application Data

(60) Provisional application No. 63/143,245, filed on Jan. 29, 2021.

(51) Int. Cl.
| | |
|---|---|
| C07D 471/04 | (2006.01) |
| C07D 401/04 | (2006.01) |
| C07D 401/14 | (2006.01) |
| C07D 405/14 | (2006.01) |

(52) U.S. Cl.
CPC ......... *C07D 471/04* (2013.01); *C07D 401/04* (2013.01); *C07D 401/14* (2013.01); *C07D 405/14* (2013.01)

(58) Field of Classification Search
CPC .. C07D 471/04; C07D 401/04; C07D 401/14; C07D 405/14; C07D 487/04; A61P 35/00
USPC ........................................................ 514/234
See application file for complete search history.

(56) References Cited

U.S. PATENT DOCUMENTS

| | | |
|---|---|---|
| 11,535,621 B2 | 12/2022 | Schenkel et al. |
| 2021/0032251 A1 | 2/2021 | Schenkel et al. |

FOREIGN PATENT DOCUMENTS

| | | |
|---|---|---|
| WO | WO 2012/075080 | 6/2012 |
| WO | WO 2013/067296 | 5/2013 |
| WO | WO 2014/159837 | 10/2014 |
| WO | WO 2016/087975 | 6/2016 |
| WO | WO 2017/053604 | 3/2017 |
| WO | WO 2018/151830 | 8/2018 |
| WO | WO 2019/020643 | 1/2019 |
| WO | WO 2021/021986 | 2/2021 |
| WO | WO 2021/087087 | 5/2021 |
| WO | WO 2021/207186 | 10/2021 |

OTHER PUBLICATIONS

Barbosa et al., "The enzyme CD38 (a NAD glycohydrolase, EC 3.2.2.5) is necessary for the development of diet-induced obesity," FASEB, 2007, J21(13):3629-3639.
Baruch et al., "Stromal CD38 regulates outgrowth of primary melanoma and generation of spontaneous metastasis," Oncotarget, 2018, 9:31797-811.
Becherer et al., "Discovery of 4-Amino-8-quinoline Carboxamides as Novel, Submicromolar Inhibitors of NAD-Hydrolyzing Enzyme CD38," J. Med. Chem. 2015, 58:7021-7056.
Bengsch et al., "Epigenomic-Guided Mass Cytometry Profiling Reveals Disease-Specific Features of Exhausted CD8 T Cells," Immunity, 2018, 48(5):1029-1045 e1025.
Berge et al., "Pharmaceutical Salts," Journal of Pharmaceutical Science, Jan. 1977, 66(1):1-19.
Blacher et al., "Inhibition of glioma progression by a newly discovered CD38 inhibitor," Int J Cancer, 2015, 136(6):1422-1433.
Bu et al., "CD38 knockout suppresses tumorigenesis in mice and clonogenic growth of human lung cancer cells," Carcinogenesis, 2017, 39(2): 242-251.
Camacho-Pereira et al., "CD38 Dictates Age-Related NAD Decline and Mitochondrial Dysfunction through an SIRT3-Dependent Mechanism," Cell Metab, 2016, 23:1127-39.
Ceni et al., "Evidence for an intracellular ADP-ribosyl cyclase/NAD+-glycohydrolase in brain from CD38-deficient mice," J Biol Chem, 2003, 278(42):40670-40678.
Chatterjee et al., "CD38-NAD + Axis Regulates Immunotherapeutic Anti-Tumor T Cell Response," Cell Metab, 2018, 27(1):85-100 e108.
Chen et al., "CD38-Mediated Immunosuppression as a Mechanism of Tumor Cell Escape from PD-1/PD-L1 Blockade," Cancer Discov, 2018, 8(9):1156-1175.
Chen et al., "Targeted disruption of CD38 accelerates autoimmune diabetes in NOD/Lt mice by enhancing autoimmunity in an ADP-ribosyltransferase 2-dependent fashion," J Immunol I, 2006, 6(8):4590-4599.
Chevrier et al., "An Immune Atlas of Clear Cell Renal Cell Carcinoma," Cell, 2017, 169(4):736-749, e718.
Chini et al., "CD38 ecto-enzyme in immune cells is induced during aging and regulates NAD+ and NMN levels," Nature Metabolism, Nov. 2020, 2:1284-1304.

(Continued)

*Primary Examiner* — Jared Barsky
*Assistant Examiner* — Liyuan Mou
(74) *Attorney, Agent, or Firm* — Fish & Richardson P.C.

(57) ABSTRACT

The present invention relates to bicyclic heterocycle compounds of Formula (I):

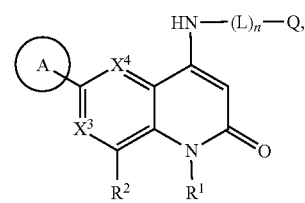

and pharmaceutically acceptable salts thereof, which are inhibitors of CD38 and are useful in the treatment of cancer.

9 Claims, 1 Drawing Sheet

(56) References Cited

OTHER PUBLICATIONS

Chini et al., "The Pharmacology of CD38/NADase: An Emerging Target in Cancer and Diseases of Aging," Trends Pharmacol Sci, 2018, 39(4): 424-436.
Covarrubias et al., "Senescent cells promote tissue NAD+ decline during ageing via the activation of CD38+ macrophages," Nature Metabolism, Nov. 2020, 2:1265-1283.
Deaglio et al., "Human CD38 (ADP-ribosyl cyclase) is a counter-receptor of CD31, an Ig superfamily member," J Immunol, 1998, 160: 395-402.
Deaton et al., "2,4-Diamino-8-quinazoline carboxamides as novel, potent inhibitors of the NAD hydrolyzing enzyme CD38: Exploration of the 2-position structure-activity relationships," Bioorganic & Medicinal Chemistry, 2018, 26(8):2107-2150.
Deshpande et al., "Altered airway responsiveness in CD38-deficient mice," Am J Respir Cell Mal Biol, 2005, 32:149-56.
Deshpande et al., "CD38 in the pathogenesis of allergic airway disease: Potential therapeutic targets," Pharmacology & Therapeutics, Apr. 2017, 172:116-126.
Feng et al., "Targeting CD38 Suppresses Induction and Function of T Regulatory Cells to Mitigate Immunosuppression in Multiple Myeloma," Clin Cancer Res, 2017, 23(15):4290-4300.
Ferretti et al., "Canonical and non-canonical adenosinergic pathways," Immunol Lett, 2019, 205:25-30.
Frerichs et al., "CD38-targeting antibodies in multiple myeloma: mechanisms of action and clinical experience," Expert Rev Clin Immunol, 2018, 14:197-206.
Fukushi et al., "Identification of cyclic ADP-ribose-dependent mechanisms in pancreatic muscarinic Ca(2+) signaling using CD38 knockout mice," J Biol Chem, 2001, 276:649-55.
Galon et al., "Approaches to treat immune hot, altered and cold tumours with combination immunotherapies," Nat Rev Drug Discov. 2019, 18(3): 197-218.
Haag, "Extracellular NAD and ATP: Partners in immune cell modulation," Purinergic Signal, 2007, 3(1-2):71-81.
Haffner et al., "Discovery, Synthesis, and Biological Evaluation of Thiazoloquin(az)olin(on)es as Potent CD38 Inhibitors," J. Med. Chem., 2015, 58:3548-3571.
Hashimoto et al., "CD8 T Cell Exhaustion in Chronic Infection and Cancer: Opportunities for Interventions," Annu Rev Med., 2018, 69:301-318.
Hay et al., "Discovery and Optimization of Small-Molecule Ligands for the CBP/p300 Bromodomains—Supporting Information," 2014, S1-S99.
Hay et al., "Discovery and Optimization of Small-Molecule Ligands for the CBP/p300 Bromodomains," Journal of the American Chemical Society, 2014, 136(26):9308-9319.
Hogan et al., "The Multi-faceted Ecto-enzyme CD38: Roles in Immunomodulation, Cancer, Aging, and Metabolic Diseases," Front Immunol, 2019, 10:1187.
Horenstein et al., "A CD38/CD203a/CD73 ectoenzymatic pathway independent of CD39 drives a novel adenosinergic loop in human T lymphocytes," Oncoimmunology, 2013, 2(9):e26246.
Hubert et al., "Extracellular NAD+ shapes the Foxp3+ regulatory T cell compartment through the ART2-P2X7 pathway," J Exp Med, 2010, 207: 2561-8.
International Preliminary Report on Patentability in International Appln. No. PCT/US2020/044156, dated Feb. 1, 2022, 8 pages.
International Search Report and Written Opinion in International Appln. No. PCT/US2020/044156, dated Oct. 15, 2020, 14 pages.
International Search Report and Written Opinion in International Appln. No. PCT/US2022/014221, dated Apr. 12, 2022, 13 pages.
Karakasheva et al., "CD38+ M-MDSC expansion characterizes a subset of advanced colorectal cancer patients," JCI Insight, 2018, 3:1-8.
Karakasheva et al., "CD38-Expressing Myeloid-Derived Suppressor Cells Promote Tumor Growth in a Murine Model of Esophageal Cancer," Cancer Res, 2015, 75(19):4074-4085.
Kato et al., "CD38 disruption impairs glucose-induced increases in cyclic ADP-ribose, [Ca2+]i, and insulin secretion," J Biol Chem, 1999, 274:1869-72.
Krejcik et al., "Daratumumab depletes CD38+ immune regulatory cells, promotes T-cell expansion, and skews T-cell repertoire in multiple myeloma," Blood, 2016, 128(3):384-394.
Langley et al., "CD38 dependent NAD+ depletion contributes to oligodendrocyte loss and inhibition of myelin regeneration," BioRxiv, Jun. 2020, 46 pages.
Lavin et al., "Innate Immune Landscape in Early Lung Adenocarcinoma by Paired Single-Cell Analyses," Cell, 2017, 169(4):750-765 e717.
Levy, "CD38 deficiency in the tumor microenvironment attenuates glioma progression and modulates features of tumor-associated microglia/macrophages," Neuro Oncol, 2012, 14(8):1037-1049.
Liao et al., "CD38 enhances the proliferation and inhibits the apoptosis of cervical cancer cells by affecting the mitochondria functions," Mol Carcinog, 2017, 56(10):2245-2257.
Lv et al., "NAD+ Metabolism Maintains Inducible PD-L1 Expression to Drive Tumor Immune Evasion," Cell Metabolism, Jan. 2021, 33(1):110-127.
Mitsui-Saito et al., "CD38 gene disruption inhibits the contraction induced by alpha-adrenoceptor stimulation in mouse aorta," J Vet Med Sci, 2003, 65:1325-30.
Partida-Sanchez et al., "Regulation of dendritic cell trafficking by the ADP-ribosyl cyclase CD38: impact on the development of humoral immunity," Immunity, 2004, 20:279-91.
Partida-Sanchez et al., "Cyclic ADP-ribose production by CD38 regulates intracellular calcium release, extracellular calcium influx and chemotaxis in neutrophils and is required for bacterial clearance in vivo," Nat Med, 2001, 7:1209-16.
Patton et al., "The PI3K p110δ regulates expression of CD38 on regulatory T cells," PLoS One, 2011, 6(3):e17359.
Peclat et al., "The NADase enzyme CD38: an emerging pharmacological target for systemic sclerosis, systemic lupus erythematosus and rheumatoid arthritis," Current opinion in rheumatology, Nov. 2020, 32(6):488-496.
Preugschat, "The base exchange reaction of NAD+ glycohydrolase: identification of novel heterocyclic alternative substrates," Fetal. Arch Biochem Biophys, 2008, 479: 114-20.
Quarona et al., "CD38 and CD157: a long journey from activation markers to multifunctional moleculesm," Cytometry B Clin Cytom, 2013, 84(4):207-217.
Sahoo et al., "Boolean analysis identifies CD38 as a biomarker of aggressive localized prostate cancer," Oncotarget, 2018, 9:6550-61.
Scully et al., "Synthesis and Evaluation of Thiazoloquinolinones with Linkers to Enable Targeting of CD38," Acs Medicinal Chemistry Letters, Feb. 2017, 8(2):196-200.
Shi et al., "Targeting CD38-dependent NAD+ metabolism to mitigate multiple organ fibrosis," iScience, Jan. 2021, 24(1):1-13.
STN International Web 20190506X160136-RBN1, 2019, 52 pages.
STN International Web 2019507X162614-RBN2, 2019, 64 pages.
STN International Web 20201118X163715-RBN3, 2020, 56 pages.
STN Registry No. 1092314-22-1, File Registry on STN, entered STN: Dec. 31, 2008, 3 pages.
Sun et al., "Disordered osteoclast formation and function in a CD38 (ADP-ribosyl cyclase)-deficient mouse establishes an essential role for CD38 in bone resorption," FASEB J, 2003, 17:369-75.
Takahashi et al., "Deficit of CD38/cyclic ADP-ribose is differentially compensated in hearts by gender," Biochem Biophys ResCommun, 2003, 312:434-40.
Van de Donk et al., "CD38 Antibodies in Multiple Myeloma: Mechanisms of Action and Modes of Resistance," Front Immunol, 2018, 9:2134.
Verma et al., "PD-1 blockade in subprimed CD8 cells induces dysfunctional PD-1+CD38hi cells and anti-PD-1 resistance," Nature Immunology, 2019, 1-19.
Wu et al., "CD38-expressing macrophages drive age-related NAD+ decline," Nature Metabolism, Nov. 2020, 2:1186-1187.
Xing et al., "Synthesis and Structure-Activity Relationship (SAR) Studies of Novel Pyrazolopyridine Derivatives as Inhibitors of Enterovirus Replication," J. Med. Chem., 2018, 61(4):1688-1703.
Zhang et al., "Prognostic Values of CD38 + CD101 + PD1 + CD8 + T Cells in Pancreatic Cancer," Immunol Invest, 2019, 48:466-79.

(56) References Cited

OTHER PUBLICATIONS

Zhao et al., "Determinants of the membrane orientation of a calcium signaling enzyme CD38," Biochim Biophys Acta, 2012, 1853(9):2095-2103.

Zhu et al., "Subcellular compartmentalization of NAD + and its role in cancer: A sereNADe of metabolic melodies," Pharmacol Ther, 2019, 200:27-41.

International Preliminary Report on Patentability in International Appln. No. PCT/US2022/014221, dated Aug. 10, 2023, 9 pages.

QUINOLINES AND AZAQUINOLINES AS INHIBITORS OF CD38

CLAIM OF PRIORITY

This application claims priority to U.S. Provisional Patent Application Ser. No. 63/143,245, filed on Jan. 29, 2021, the entire contents of which are hereby incorporated by reference.

FIELD OF THE INVENTION

The present invention relates to compounds which are inhibitors of CD38 and are useful in the treatment of cancer.

BACKGROUND OF THE INVENTION

CD38 (cluster of differentiation 38) is a member of the ADP-ribosyl cyclase family that is widely expressed on the surface of multiple cell types and is responsible for the degradation of nicotinamide adenine dinucleotide ($NAD^+$). CD38 was first characterized as a surface antigen on immune cells as an activation marker, located on the plasma membrane and on the membranes of intracellular organelles (Quarona, V., et al. *Cytometry B Clin Cytom* 84(4): 207-217 (2013)). Human CD38 contains 300 amino acid residues comprising a short N-terminal fragment, a single-pass transmembrane helix, and a C-terminal catalytic domain. CD38 is generally classified as a type II membrane protein; however, it has also been reported as existing in a type III orientation (Zhao YZ et al. *Biochim Biophys Acta* 1853(9): 2095-2103 (2012)). CD38 converts $NAD^+$ to ADP-ribose (ADPR) or cyclic ADPR (cADPR) and nicotinamide (Chini EN et al. *Trends Pharmacol Sci* 39(4): 424-436 (2018)). While $NAD^+$ is recognized as the major substrate for CD38, it is also known to have other substrates such as nicotinamide adenine dinucleotide phosphate ($NADP^+$) and nicotinamide mononucleotide ($NMN^+$). Under some conditions, CD38 can also catalyze base exchange reactions with these same substrates (Preugschat, F et al. *Arch Biochem Biophys*, 479: 114-20 (2008)). This CD38-dependent $NAD^+$ metabolism regulates levels of extracellular and intracellular metabolites, intracellular $Ca^{2+}$, and signal transduction pathways (Horenstein, A L, et al. *Oncoimmunology* 2(9): e26246 (2013)); Chini E N et al. 2018). CD38 also functions as a receptor, and the receptor-ligand activity of CD38 regulates development, activation, and differentiation of multiple immune cell types (Quorona B et al. 2013), and CD31/PECAM-1 has been reported to be a ligand for CD38 (Deaglio S, *J Immunol*, 160: 395-402 (1998)).

CD38 exerts diverse physiological functions, and characterization of CD38 knockout (KO) mice has clarified the various roles played by this protein. CD38 KO mice are characterized by large decreases in endogenous cADPR levels in all tissues/organs analyzed except the brain (Partida-Sanchez S et al. *Nat Med*, 7: 1209-16 (2001); Ceni C et al. *J Biol Chem* 278(42): 40670-40678 (2003)) In the pancreatic islets, loss of CD38 impairs glucose-induced production of cADPR, intracellular $Ca^{2+}$, and insulin secretion (Kato J et al. *J Biol Chem*, 274: 1869-72 (1999)). CD38 KO also impairs acetylcholine-induced accumulation of cADPR in acinar cells, leading to marked alteration of $Ca^{2+}$ signaling patterns (Fukushi Y et al. *J Biol Chem*, 276: 649-55 (2001)). Likewise, in neutrophils, cADPR production has been shown to regulate both intracellular $Ca^{2+}$ release and extracellular $Ca^{2+}$ influx during chemotaxis and is required for bacterial clearance in vivo (Partida-Sanchez S et al. *Nat Med*, 7: 1209-16 (2001)). CD38 KO mice also show other defects, including disordered osteoclast formation and function (Sun L et al. *FASEB J*, 17: 369-75 (2003)), altered airway responsiveness (Deshpande D A et al. *Am J Respir Cell Mol Biol*, 32: 149-56 (2005)), impairment of dendritic cell trafficking and reduced humoral immune response (Partida-Sanchez S et al. *Immunity*, 20: 279-91 (2004)), inhibition of α-adrenoceptor-stimulated contraction in the aorta (Mitsui-Saito M et al. *J Vet Med Sci*, 65: 1325-30 (2003)), and cardiac hypertrophy (Takahashi J et al. *Biochem Biophys Res Commun*, 312: 434-40 (2003)). These findings clearly demonstrate the diverse biological roles played by CD38.

CD38 expression has also been associated with the immunosuppressive functions of regulatory T (Treg) cells, tumor-associated macrophages (TAMs) and myeloid-derived suppressive cells (MDSCs) (Feng X et al. *Clin Cancer Res* 23(15): 4290-4300 (2017); Krejcik J et al. *Blood* 128(3): 384-394 (2016); Chevrier S et al. *Cell* 169(4): 736-749 e718 (2017); Levy A *Neuro Oncol* 14(8): 1037-1049 (2012)). CD38 KO Treg cells are remarkably sensitive to $NAD^+$-induced cell death due to their inability to consume $NAD^+$ (Chen J et al. *J Immunol* 176(8): 4590-4599 (2006); Hubert, S B et al. *J Exp Med*, 207: 2561-8 (2010)). Conversely, Tregs with high CD38 expression are more suppressive than other subsets with lower or no CD38 expression (Krejcik et al. 2016; Patton D T et al. *PLoS One* 6(3): e17359 (2011)). Likewise, $CD38^{high}$ MDSCs possess greater capacity to suppress activated T cells. The activity of such $CD38^{high}$ MDSCs promoted esophageal tumor growth in mice, an effect that could be inhibited by CD38 blockade (Karakasheva T A et al. *Cancer Res* 75(19): 4074-4085 (2015)). The expansion of functional $CD38^+$ MDSCs has also been described in colorectal cancer, especially in patients who have previously undergone therapy (Karakasheva T A et al. *JCI Insight* 3(6) (2018)). Broad systems immunology approaches have revealed the association of CD38-expressing tumor-infiltrating lymphocytes (TILs) with poor prognosis in clear cell renal cell carcinoma (ccRCC) and early lung adenocarcinoma (Chevrier S et al. 2017; Lavin Y et al. *Cell* 169(4): 750-765 e717 (2017)). In ccRCC, it was determined that CD38 was co-expressed with other markers of T cell exhaustion, whereas in lung adenocarcinoma, $CD38^{high}$ Treg cells were enriched in the tumor microenvironment (TME) (Chevrier S et al. 2017; Lavin Y et al. 2017). High co-expression of CD38 and CD101 on TILs in tumor tissue was correlated with poor survival of pancreatic cancer patients (Zhang M et al. *Immunol Invest*, 48: 466-79 (2019)). A study looking into exhausted T cell populations in humans with chronic infection and various cancers identified CD38 as a T cell exhaustion marker, and the presence of such exhausted T cells was linked to more severe disease from HIV infection and dysfunctional TILs in lung cancer (Bengsch B et al. *Immunity* 48(5): 1029-1045 e1025 (2018)). CD38 also dictates the metabolic fitness of T cells, and the inhibition of CD38 expression on T cells upregulates $NAD^+$ and activates T cells by promoting glutaminolysis, enhancing oxidative phosphorylation, and altering mitochondrial dynamics (Chatterjee S et al. 2018). This study further demonstrated that inhibition of CD38 prevented T cell exhaustion and thereby boosted the efficacy of adoptive T cell therapy (Chatterjee S et al. *Cell Metab* 27(1): 85-100 e108 (2018)).

The role of CD38 in tumorigenesis and immune suppression is an active field of research, with multiple studies associating CD38 with tumor progression. CD38 was shown to promote cervical cancer cell growth by reducing levels of reactive oxygen species and inhibiting apoptosis (Liao S et al. *Mol Carcinog* 56(10): 2245-2257 (2017)), and loss of CD38 in human lung adenocarcinoma cells inhibited cell growth, invasion, and xenograft growth in nude mice (Bu X et al. *Carcinogenesis* 39(2): 242-251 (2017)). CD38 KO mice are more resistant to tumor growth and were shown to efficiently reject B16-F10 melanoma tumors (Baruch B B et al. *Oncotarget*, 9: 31797-811 (2018)). Similarly, targeting CD38 expression or its activity in the TME inhibited glioma progression and prolonged the lifespan of glioma-bearing mice (Blacher E et al. *Int J Cancer* 136(6): 1422-1433 (2013)). CD38 has also been identified as a biomarker of aggressive localized prostate cancer (Sahoo D et al. *Oncotarget*, 9: 6550-61 (2018)).

Recent research has investigated the role of CD38 in an ecto-enzyme cascade that generates immunosuppressive adenosine from $NAD^+$. In addition to CD38, this cascade includes ectonucleotide pyrophosphatase/phosphodiesterase 1 (ENPP1) and the 5'-ectonucleotidase CD73. CD38 generates ADPR that is further hydrolyzed by ENPP1 to produce AMP, and the subsequent conversion of AMP to adenosine is regulated by CD73 (Ferretti E et al. *Immunol Lett* 205: 25-30 (2019)). This non-canonical adenosine generation pathway, which relies on CD38, occurs independently of ATP, and bypasses CD39 (Horenstein AL et al. 2013), plays a major role in creating an immunosuppressive TME, wherein dying cells provide $NAD^+$ that is eventually converted to adenosine (Haag F et al. *Purinergic Signal* 3(1-2): 71-81 (2007); Zhu Y et al. *Pharmacol Ther* 200: 27-41 (2019)).

Furthermore, a recent study demonstrated that cancer cells acquire resistance to immune checkpoint inhibitors that target programmed cell death protein 1 (PD-1) or its ligand (PD-L1) via upregulation of CD38, which blocks $CD8^+$ T cell function through adenosine receptor signaling (Chen L et al. *Cancer Discov* 8(9): 1156-1175 (2018)). CD38 blockade subsequently restored $CD8^+$ T cell proliferation, antitumor cytokine secretion, and cytotoxic capabilities. Pathologic analysis of lung cancer specimens revealed positive immunohistochemical staining for CD38 on tumor cells in 15-23% of cases, and bioinformatic analyses of datasets from non-small cell lung cancer (NSCLC) and melanoma patients revealed a strong correlation between CD38 expression and an inflamed TME (Chen L et al. 2018).

CD38 is one of the main enzymes responsible for the age-related $NAD^+$ decline that occurs in mammals (Hogan KA et al. Front Immunol 10: 1187 (2019)). CD38 KO mice are consistently protected from this progressive deficit and age-related metabolic dysfunction (Camacho-Pereira J et al. *Cell Metab*, 23: 1127-39 (2016)). Inhibition of CD38 likewise reversed age-related $NAD^+$ decline and ameliorated several metabolic, structural, and molecular features of aging in chronologically aged and progeroid mice (Camacho-Pereira J et al. 2016). CD38 KO mice are also protected from diet-induced obesity, liver steatosis, and glucose intolerance due to enhanced energy expenditure (Barbosa M T et al. *FASEB J* 21(13): 3629-3639 (2007)). Recent studies tied the age-related $NAD^+$ decline with CD38 expression on M1-like macorphages. CD38 induction in M1-like macrophages by senescence-associated inflammation led to age-related $NAD^+$ decline (Chini et al. *Nat. Metab* 11:1284-1304 (2020); Covarrubias et al. *Nat. Metab* 11:1265-1283 (2020)). This new understanding of CD38 regulation in Ml-like macrophages during ageing establishes CD38 as an attractive target to prevent age-related $NAD^+$ decline, particularly in tissues with high resident macrophage populations (Wu et al. *Nat. Metab*, 11:1186-1187 (2020)).

Consistent with the role of optimal $NAD^+$ levels and its regulation, $NAD^+$ repletion or boosting via CD38 inhibition or NAD precursor supplements can change disease outcome. $NAD^+$ replenishment with suppliments sensitizes anti-PD-L1 therapy-resistant tumors to immunotherapy and CD38 expressing tumors were shown to be resisitant to immunotherapy. (Lv et al. *Cell Metab*, 33: P110-127 (2021)). This further reinforces the rationale for CD38 inhibtion in immunotherapy resistant patients. Further, using genetic and pharmacological approaches it was demonstrated that targeting CD38-dependent $NAD^+$ metabolism could mitigate multiple organ fibrosis. (Shi et al. iScience, 24: (2021)). CD38 is elevated in skin biopsies of patients with systemic sclerosis. Boosting $NAD^+$ levels by CD38 inhibition or supplements prevented multi-organ fibrosis.

CD38 is a cell-surface marker for multiple myeloma and these cells are specifically susceptible to CD38 depletion, thus CD38 offers a useful therapeutic target for this malignancy (Chini E N et al. 2018). Clinical trials have demonstrated that CD38-targeting antibodies are specifically effective in relapsed/refractory multiple myeloma patients (Frerichs K A et al. *Expert Rev Clin Immunol*, 14: 197-206 (2018); van de Donk N W C J et al. *Front Immunol*, 9: 2134 (2018)), and the anti-CD38 antibody daratumumab has been approved by the FDA for multiple myeloma treatment. Several other therapeutic antibodies against CD38 are now in clinical development for multiple myeloma and other cancers (van de Donk N W C J 2018).

The literature is replete with references reporting the potential therapeutic benefits of inhibiting abnormal expression or activity of CD38. For example, the following diseases are characterized by abnormal expression or activity of CD38: non-small cell lung cancer, melanoma, checkpoint therapy treated and/or resistant cancers, and adenosine-dependent tumors (Chen L et al. "CD38-mediated immunosuppression as a mechanism of tumor cell escape from PD-1/PD-L1 blockade." *Cancer Discov.* 8, 1156-1175 (2018)); lung cancer (adenocarcinoma) (Bu X et al. "CD38 knockout suppresses tumorigenesis in mice and clonogenic growth of human lung cancer cells." *Carcinogenesis* 39, 242-251 (2018)); cervical cancer (Liao S et al. "CD38 enhances the proliferation and inhibits the apoptosis of cervical cancer cells by affecting the mitochondria functions." *Mol. Carcinog.* 56, 2245-2257 (2017)); glioma (Blacher E et al. "Inhibition of glioma progression by a newly discovered CD38 inhibitor." *Int. J. Cancer* 136, 1422-1433 (2015)); colorectal cancer (Karakasheva T A et al. "$CD38^+$ M-MDSC expansion characterizes a subset of advanced colorectal cancer patients." *JCI Insight* 3, 1-8 (2018)); esophageal cancer (Karakasheva T A et al. "CD38-expressing myeloid-derived suppressor cells promote tumor growth in a murine model of esophageal cancer." *Cancer Res.* 75, 4074-4085 (2015)); clear cell renal cell carcinoma (Chevrier S et al. "An immune atlas of clear cell renal cell carcinoma." *Cell* 169, 736-749 (2017)); prostate cancer (Sahoo D et al. "Boolean analysis identifies CD38 as a biomarker of aggressive localized prostate cancer." *Oncotarget* 9, 6550-6561 (2018)); treg-infiltrated tumors (Lavin Y et al. "Innate immune landscape in early lung adenocarcinoma by paired single-cell analyses." *Cell* 169, 750-757.e15 (2017)); MDSC-infiltrated tumors (Karakasheva T A et al. "$CD38^+$ M-MDSC expansion characterizes a subset of advanced colorectal cancer patients." *JCI Insight* 3, 1-8 (2018)); HIV/AIDS (Bengsch B et al. "Epigenomic-guided mass cytometry profiling reveals disease-specific features of exhausted resource epigenomic-guided mass cytometry profiling reveals disease-specific features of exhausted CD8 T cells." *Cell* 48, 1029-1045 (2018)); adoptive T cell therapy (Chatterjee S et al. "CD38-NAD+ axis regulates immunotherapeutic anti-tumor T cell response." *Cell Metab.* 27, 85-100.e8 (2018)); pancreatic cancer (Zhang M et al. "Prognostic values of CD38+CD101+PD1+CD8+ T cells in pancreatic cancer." *Immunol. Invest.* 48, 466-479 (2019)); and multiple myeloma (Chini E N et al. "The Pharmacology of CD38/NADase: An Emerging Target in Cancer and Diseases of Aging." *Trends Pharmacol. Sci.* 39, 424-436 (2018)). Age related ailments (Wu et.al. "CD38-expressing macrophages drive age-related NAD(+) decline" *Nat Metab.* 11 (2020)); Multiple organ fibrosis, Systemic sclerosis, Metabolic Diseases (Shi et al. "Targeting CD38-dependent NAD+ metabolism to mitigate multiple organ fibrosis" *iScience*, 24: (2021)); systemic lupus erythematosus (Peclat et al. "The NADase enzyme CD38: an emerging pharmacological target for systemic sclerosis, systemic lupus erythematosus and rheumatoid arthritis" *Curr Opin Rheumatol.* (2020); Asthma, allergic airway disease (Deshpande et al. "CD38 in the pathogenesis of allergic airway disease: potential therapeutic targets" *Pharmacol Ther.*, (2016)); Multiple sclerosis, neurodegenration, neurological diseases (Langley et.al "CD38 dependent NAD+ depletion contributes to oligodendrocyte loss and inhibition of myelin regeneration" *BioRxiv* (2020)).

In summation, CD38 is a multifunctional enzyme and signaling receptor that plays important functions in cancer progression, the creation of an immunosuppressive TME, metabolic fitness of T cells, and the modulation of NAD+ levels in aging and other physiological conditions. The inhibition of CD38 in various disease states—including tumor growth—has already shown clinical promise, and the development of potent and selective small-molecule inhibitors will create therapeutic options for other conditions characterized by abnormal expression or activity of CD38. The compounds, compositions, and methods described herein will help meet these and other needs.

SUMMARY OF THE INVENTION

The present invention provides a compound of Formula I:

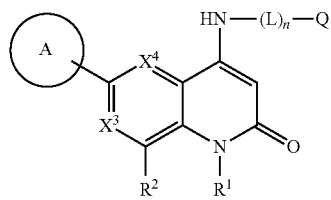

or a pharmaceutically acceptable salt thereof, wherein constituent members are defined herein.

The present invention is also directed to a pharmaceutical composition comprising a compound of Formula I, or a pharmaceutically acceptable salt thereof, and at least one pharmaceutically acceptable carrier.

The present invention is also directed to a method of inhibiting a function of CD38 by contacting the CD38 with a compound of Formula I, or a pharmaceutically acceptable salt thereof.

The present invention is also directed to a method of treating a disease associated with abnormal activity or expression of CD38 by administering a therapeutically effective amount of a compound of Formula I, or a pharmaceutically acceptable salt thereof, to a patient in need thereof.

The present invention is further directed to a compound of the invention, or a pharmaceutically acceptable salt thereof, for use in the treatment of a disease associated with abnormal activity or expression of CD38.

The present invention is further directed to use of a compound of the invention, or a pharmaceutically acceptable salt thereof, in the manufacture of a medicament for use in therapy.

DETAILED DESCRIPTION

Figure 1B:
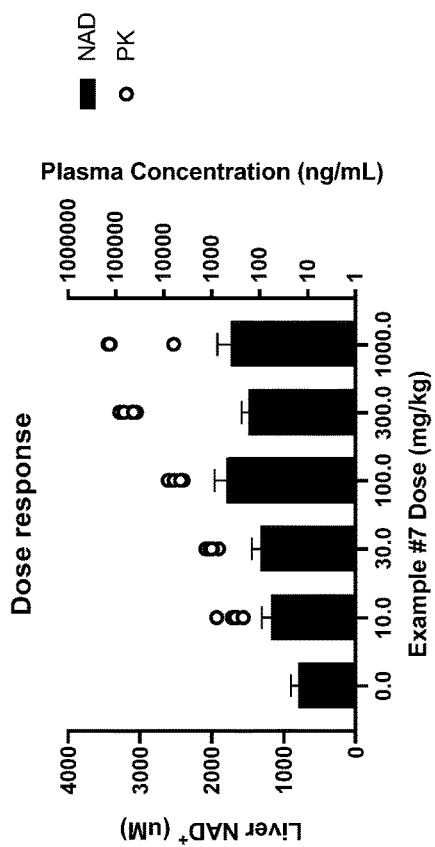
FIG. 1B is a graph of the concentration of NAD+ in the liver at a single time point after dosing with various amounts of the compound of Example 7.

The present invention relates to a CD38-inhibiting compound of Formula I:

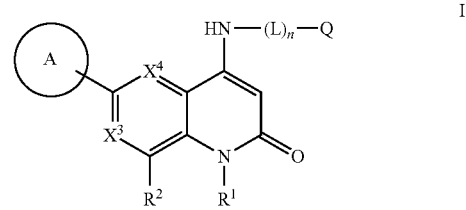

or a pharmaceutically acceptable salt thereof, wherein:
  $X^3$ is $CR^3$ or N;
  $X^4$ is $CR^4$ or N;
  A is a 5-membered heteroaryl group having 1, 2 or 3 ring-forming heteroatoms selected from N, O, and S, wherein the 5-membered heteroaryl group of A is optionally substituted by 1, 2, or 3 substituents independently selected from halo and $C_{1-4}$ alkyl;
  L is a $C_{1-4}$ alkylene linker;
  n is 0 or 1;
  Q is H, $C_{1-10}$ alkyl, $C_{2-10}$ alkenyl, $C_{2-10}$ alkynyl, $C_{1-10}$ haloalkyl, $C_{6-10}$ aryl, $C_{3-14}$ cycloalkyl, 5-14 membered heteroaryl, or 4-14 membered heterocycloalkyl, wherein said $C_{1-10}$ alkyl, $C_{2-10}$ alkenyl, $C_{2-10}$ alkynyl, $C_{1-10}$ haloalkyl, $C_{6-10}$ aryl, $C_{3-14}$ cycloalkyl, 5-14 membered heteroaryl, and 4-14 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, and $C_{2-6}$ alkynyl are optionally substituted by 1, 2, or 3 substituents independently selected from $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

each Cy$^1$ is independently selected from C$_{6-10}$ aryl, C$_{3-7}$ cycloalkyl, 5-10 membered heteroaryl, and 4-10 membered heterocycloalkyl, each optionally substituted by 1, 2, 3, or 4 substituents independently selected from halo, C$_{1-6}$ alkyl, C$_{2-6}$ alkenyl, C$_{2-6}$ alkynyl, C$_{1-6}$ haloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

R$^1$ is C$_{1-6}$ alkyl;

R$^2$, R$^3$, and R$^4$ are each independently selected from H, halo, C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$, wherein said C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of R$^2$, R$^3$, and R$^4$ are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a2}$, SR$^{a2}$, C(O)R$^{b2}$, (O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

each R$^a$, R$^b$, R$^c$, R$^d$, R$^{a1}$, R$^{b1}$, R$^{c1}$, R$^{d1}$, R$^{a2}$, R$^{b2}$, R$^{c2}$, and R$^{d2}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of R$^a$, R$^b$, R$^c$, R$^d$, R$^{a1}$, R$^{b1}$, R$^{c1}$, R$^{d1}$, R$^{a2}$, R$^{b2}$, R$^{c2}$, and R$^{d2}$ is optionally substituted with 1, 2, 3, 4, or 5 substituents independently selected from halo, C$_{1-4}$ alkyl, C$_{1-4}$ haloalkyl, C$_{1-6}$ haloalkyl, C$_{2-6}$ alkenyl, C$_{2-6}$ alkynyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

or R$^c$ and R$^d$ together with the N atom to which they are attached form a 4-7 membered heterocycloalkyl group optionally substituted with 1, 2, or 3 substituents independently selected from halo, C$_{1-4}$ alkyl, C$_{1-4}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

or R$^{c1}$ and R$^{d1}$ together with the N atom to which they are attached form a 4-7 membered heterocycloalkyl group optionally substituted with 1, 2, or 3 substituents independently selected from halo, C$_{1-4}$ alkyl, C$_{1-4}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

or R$^{c2}$ and R$^{d2}$ together with the N atom to which they are attached form a 4-7 membered heterocycloalkyl group optionally substituted with 1, 2, or 3 substituents independently selected from halo, C$_{1-4}$ alkyl, C$_{1-4}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

each R$^{a3}$, R$^{b3}$, R$^{c3}$, and R$^{d3}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-6 membered heteroaryl, and 4-7 membered heterocycloalkyl, wherein said C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-6 membered heteroaryl, and 4-7 membered heterocycloalkyl are each optionally substituted with 1, 2, or 3 substituents independently selected from OH, CN, amino, halo, C$_{1-6}$ alkyl, C$_{1-6}$ alkoxy, C$_{1-6}$ haloalkyl, and C$_{1-6}$ haloalkoxy; and each R$^e$, R$^{e1}$, R$^{e2}$, and R$^{e3}$ is independently selected from H, C$_{1-4}$ alkyl, and CN;

wherein when X$^3$ is CR$^3$ and X$^4$ is CR$^4$, then Ring A is not

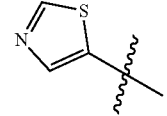

In some embodiments, A is a 5-membered heteroaryl group having 1, 2 or 3 ring-forming N atoms, wherein the 5-membered heteroaryl group of A is optionally substituted by 1, 2, or 3 substituents independently selected from halo and C$_{1-4}$ alkyl.

In some embodiments, A is a 5-membered heteroaryl group having 1, 2 or 3 ring-forming heteroatoms selected from N, O, and S.

In some embodiments, A is imidazolyl or thiazolyl, optionally substituted by 1, 2, or 3 substituents independently selected from halo and C$_{1-4}$ alkyl. In some embodiments, A is imidazolyl optionally substituted by 1, 2, or 3 substituents independently selected from halo and C$_{1-4}$ alkyl. In some embodiments, A is thiazolyl optionally substituted by 1, 2, or 3 substituents independently selected from halo and $C_{1-4}$ alkyl.

In some embodiments, A is imidazolyl or thiazolyl. In some embodiments, A is imidazolyl. In some embodiments, A is thiazolyl.

In some embodiments, A is imidazol-1-yl or thiazol-5-yl. In some embodiments, A is imidazol-1-yl. In some embodiments, A is thiazol-5-yl.

In some embodiments, A is

In some embodiments, A is

In some embodiments, $X^3$ is $CR^3$.
In some embodiments, $X^3$ is N.
In some embodiments, $X^4$ is $CR^4$.
In some embodiments, $X^4$ is N.
In some embodiments, $R^1$ is methyl.
In some embodiments, $R^2$ is selected from H, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

In some embodiments, $R^2$ is H, halo, or $C_{1-4}$ alkyl.
In some embodiments, $R^2$ is H.
In some embodiments, $R^3$ is selected from H, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

In some embodiments, $R^3$ is H, halo, or $C_{1-4}$ alkyl.
In some embodiments, $R^3$ is H.
In some embodiments, $R^4$ is selected from H, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

In some embodiments, $R^4$ is H, halo, or $C_{1-4}$ alkyl.
In some embodiments, $R^4$ is H.
In some embodiments, Q is $C_{6-10}$ aryl, $C_{3-14}$ cycloalkyl, 5-14 membered heteroaryl, or 4-14 membered heterocycloalkyl, wherein said $C_{6-10}$ aryl, $C_{3-14}$ cycloalkyl, 5-14 membered heteroaryl, and 4-14 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, and $C_{2-6}$ alkynyl are optionally substituted by 1, 2, or 3 substituents independently selected from $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, Q is phenyl, $C_{3-6}$ cycloalkyl, 5-6 membered heteroaryl, or 4-6 membered heterocycloalkyl, wherein said phenyl, $C_{3-6}$ cycloalkyl, 5-6 membered heteroaryl, and 4-6 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, and $C_{2-6}$ alkynyl are optionally substituted by 1, 2, or 3 substituents independently selected from $Cy^1$, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, Q is $C_{6-10}$ aryl, $C_{3-14}$ cycloalkyl, 5-14 membered heteroaryl, or 4-14 membered heterocycloalkyl, wherein said $C_{6-10}$ aryl, $C_{3-14}$ cycloalkyl, 5-14 membered heteroaryl, and 4-14 membered heterocycloalkyl of Q are each optionally substituted with 1, 2, or 3 substituents independently selected from $Cy^1$, halo, $C_{1-6}$ alkyl, $C_{1-6}$ haloalkyl, CN, $OR^a$, $NR^cR^d$, and $S(O)_2R^b$, wherein said $C_{1-6}$ alkyl is optionally substituted by $OR^a$.

In some embodiments, Q is $C_{3-14}$ cycloalkyl optionally substituted with 1, 2, or 3 substituents independently selected from $Cy^1$, halo, $C_{1-6}$ alkyl, $C_{1-6}$ haloalkyl, CN, $OR^a$, $NR^cR^d$, and $S(O)_2R^b$, wherein said $C_{1-6}$ alkyl is optionally substituted by $OR^a$.

In some embodiments, Q is 5-14 membered heteroaryl optionally substituted with 1, 2, or 3 substituents independently selected from $Cy^1$, halo, $C_{1-6}$ alkyl, $C_{1-6}$ haloalkyl, CN, $OR^a$, $NR^cR^d$, and $S(O)_2R^b$, wherein said $C_{1-6}$ alkyl is optionally substituted by $OR^a$.

In some embodiments, Q is $C_{3-6}$ cycloalkyl optionally substituted with 1, 2, or 3 substituents independently selected from $Cy^1$, halo, $C_{1-6}$ alkyl, $C_{1-6}$ haloalkyl, CN, $OR^a$, $NR^cR^d$, and $S(O)_2R^b$, wherein said $C_{1-6}$ alkyl is optionally substituted by $OR^a$.

In some embodiments, Q is 5-6 membered heteroaryl optionally substituted with 1, 2, or 3 substituents independently selected from $Cy^1$, halo, $C_{1-6}$ alkyl, $C_{1-6}$ haloalkyl, CN, $OR^a$, $NR^cR^d$, and $S(O)_2R^b$, wherein said $C_{1-6}$ alkyl is optionally substituted by $OR^a$.

In some embodiments, Q is phenyl, $C_{3-6}$ cycloalkyl, 5-6 membered heteroaryl, or 4-6 membered heterocycloalkyl, wherein said phenyl, $C_{3-6}$ cycloalkyl, 5-6 membered heteroaryl, and 4-6 membered heterocycloalkyl of Q are each optionally substituted with 1, 2, or 3 substituents independently selected from $Cy^1$, halo, $C_{1-6}$ alkyl, $C_{1-6}$ haloalkyl, CN, $OR^a$, $NR^cR^d$, and $S(O)_2R^b$, wherein said $C_{1-6}$ alkyl is optionally substituted by $OR^a$.

In some embodiments, Q is $C_{3-6}$ cycloalkyl or 4-6 membered heterocycloalkyl, wherein said $C_{3-6}$ cycloalkyl and 4-6 membered heterocycloalkyl of Q are each optionally substituted with 1, 2, or 3 substituents independently selected from $Cy^1$, halo, $C_{1-6}$ alkyl, $C_{1-6}$ haloalkyl, CN, $OR^a$, $NR^cR^d$, and $S(O)_2R^b$, wherein said $C_{1-6}$ alkyl is optionally substituted by $OR^a$.

In some embodiments, Q is phenyl or 5-6 membered heteroaryl, wherein said phenyl and 5-6 membered heteroaryl of Q are each optionally substituted with 1, 2, or 3 substituents independently selected from $Cy^1$, halo, $C_{1-6}$ alkyl, $C_{1-6}$ haloalkyl, CN, $OR^a$, $NR^cR^d$, and $S(O)_2R^b$, wherein said $C_{1-6}$ alkyl is optionally substituted by $OR^a$.

In some embodiments, Q is cyclohexyl, phenyl, pyridinyl, or piperidinyl, each optionally substituted with 1 or 2 substituents independently selected from $Cy^1$, halo, $C_{1-6}$ alkyl, $C_{1-6}$ haloalkyl, CN, $OR^a$, $NR^cR^d$, and $S(O)_2R^b$, wherein said $C_{1-6}$ alkyl is optionally substituted by $OR^a$.

In some embodiments, Q is cyclohexyl optionally substiuted with 1 or 2 substituents independently selected from $Cy^1$, halo, $C_{1-6}$ alkyl, $OR^a$, and $NR^cR^d$, wherein said $C_{1-6}$ alkyl is optionally substituted by $OR^a$.

In some embodiments, Q is phenyl optionally substituted with $C_{1-6}$ haloalkyl or CN.

In some embodiments, Q is pyridinyl optionally substituted with $OR^a$.

In some embodiments, Q is piperidinyl optionally substituted with $S(O)_2R^b$.

In some embodiments, Q is cyclohexyl substiuted with 1 or 2 substituents independently selected from $Cy^1$, halo, $C_{1-6}$ alkyl, $OR^a$, and $NR^cR^d$, wherein said $C_{1-6}$ alkyl is optionally substituted by $OR^a$.

In some embodiments, Q is phenyl substituted with $C_{1-6}$ haloalkyl or CN.

In some embodiments, Q is pyridinyl substituted with $OR^a$.

In some embodiments, Q is piperidinyl substituted with $S(O)_2R^b$.

In some embodiments, Q is selected from 4-(2-methoxyethoxy)cyclohexyl, 4-(oxetan-3-ylamino)cyclohexyl, 4-(2-hydroxypropan-2-yl)cyclohexyl, 4-((2,2,2-trifluoroethyl)amino)cyclohexyl, 4-(2-(dimethylamino)-2-oxoethoxy)cyclohexyl, 4-((2,2-difluoropropyl)amino)cyclohexyl, 4-(2-(pyrrolidin-1-yl)ethoxy)cyclohexyl, 4-((2,2-difluoropropyl)amino)cyclohexyl, 1-hydroxyethyl)cyclohexyl, 4-(2-(dimethylamino)-2-oxoethoxy)cyclohexyl, 4-((2,2,2-trifluoroethyl)amino)cyclohexyl, 4-methoxycyclohexyl, 4,4-difluorocyclohexyl, 4-(1-hydroxycyclopropyl)cyclohexyl, 4-(trifluoromethyl)phenyl, 4-cyanophenyl, 6-(2-morpholinoethoxy)pyridin-3-yl, 6-(2,2,2-trifluoroethoxy)pyridin-3-yl, 6-(2-(dimethylamino)ethoxy)pyridin-3-yl, 6-(2-(pyrrolidin-1-yl)ethoxy)pyridin-3-yl, and 1-(methyl sulfonyl)piperidin-4-yl.

In some embodiments, Q is selected from 4-(2-methoxyethoxy)cyclohexyl, 4-(oxetan-3-ylamino)cyclohexyl, 4-(2-hydroxypropan-2-yl)cyclohexyl, 4-((2,2,2-trifluoroethyl)amino)cyclohexyl, 4-(2-(dimethylamino)-2-oxoethoxy)cyclohexyl, 4-((2,2-difluoropropyl)amino)cyclohexyl, 4-(2-(pyrrolidin-1-yl)ethoxy)cyclohexyl, 4-((2,2-difluoropropyl)amino)cyclohexyl, 1-hydroxyethyl)cyclohexyl, 4-(2-(dimethylamino)-2-oxoethoxy)cyclohexyl, 4-((2,2,2-trifluoroethyl)amino)cyclohexyl, 4-methoxycyclohexyl, 4,4-difluorocyclohexyl, and 4-(1-hydroxycyclopropyl)cyclohexyl.

In some embodiments, Q is selected from 4-(trifluoromethyl)phenyl and 4-cyanophenyl.

In some embodiments, Q is selected from 6-(2-morpholinoethoxy)pyridin-3-yl, 6-(2,2,2-trifluoroethoxy)pyridin-3-yl, 6-(2-(dimethylamino)ethoxy)pyridin-3-yl, and 6-(2-(pyrrolidin-1-yl)ethoxy)pyridin-3-yl.

In some embodiments, Q is 1-(methyl sulfonyl)piperidin-4-yl.

In some embodiments, each $Cy^1$ is independently selected from $C_{3-7}$ cycloalkyl optionally substituted by 1 or 2 substituents independently selected from $OR^a$.

In some embodiments, each $Cy^1$ is cyclopropyl optionally substituted by 1 or 2 substituents independently selected from $OR^a$.

In some embodiments, $Cy^1$ is 1-hydroxycyclopropyl.

In some embodiments, each $R^a$ is independently selected from H, $C_{1-6}$ alkyl, $C_{1-6}$ haloalkyl, and 4-10 membered heterocycloalkyl-$C_{1-4}$ alkyl, wherein said $C_{1-6}$ alkyl of $R^a$ is optionally substituted with 1, 2, 3, 4, or 5 substituents independently selected from $OR^{a3}$, $C(O)NR^{c3}R^{d3}$, and $NR^{c3}R^{d3}$.

In some embodiments, each $R^c$ and $R^d$ is independently selected from H, $C_{1-6}$ alkyl, $C_{1-6}$ haloalkyl, and 4-10 membered heterocycloalkyl.

In some embodiments, each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, and $C_{1-6}$ haloalkyl.

In some embodiments, each $R^{a3}$, $R^{b3}$, $R^{c3}$, and $R^{d3}$ is independently selected from H, $C_{1-6}$ alkyl, and $C_{1-6}$ haloalkyl.

In some embodiments, n is 0.

In some embodiments, provided herein is a compound having Formula II:

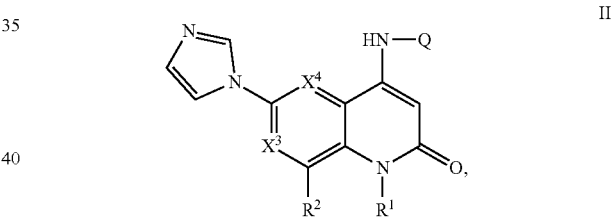

or a pharmaceutically acceptable salt thereof, wherein $R^1$, $R^2$, $X^3$, $X^4$, and Q are as defined herein.

In some embodiments, provided herein is a compound having Formula III:

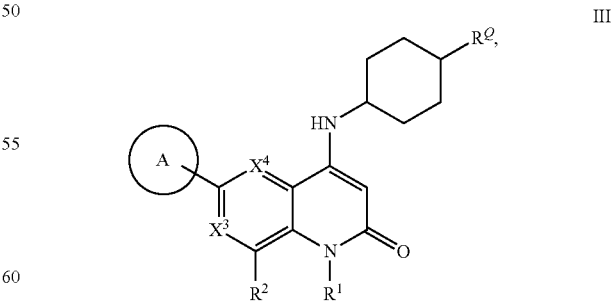

or a pharmaceutically acceptable salt thereof, wherein $R^Q$ is selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)$ R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$, wherein said C$_{1-6}$ alkyl, C$_{2-6}$ alkenyl, and C$_{2-6}$ alkynyl are optionally substituted by 1, 2, or 3 substituents independently selected from Cy$^1$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

In some embodiments, R$^Q$ is selected from Cy$^1$, halo, C$_{1-6}$ alkyl, OR$^a$, and NR$^c$R$^d$, wherein said C$_{1-6}$ alkyl is optionally substituted by OR$^a$ In some embodiments, provided herein is a compound of Formula (I), wherein:
X$^3$ is CR$^3$ or N;
X$^4$ is CR$^4$ or N;
A is a 5-membered heteroaryl group having 1, 2 or 3 ring-forming N atoms, wherein the 5-membered heteroaryl group of A is optionally substituted by 1, 2, or 3 substituents independently selected from halo and C$_{1-4}$ alkyl;
n is 0;
Q is phenyl, C$_{3-6}$ cycloalkyl, 5-6 membered heteroaryl, or 4-6 membered heterocycloalkyl, wherein said phenyl, C$_{3-6}$ cycloalkyl, 5-6 membered heteroaryl, and 4-6 membered heterocycloalkyl of Q are each optionally substituted with 1, 2, or 3 substituents independently selected from Cy$^1$, halo, C$_{1-6}$ alkyl, C$_{1-6}$ haloalkyl, CN, OR$^a$, NR$^c$R$^d$, and S(O)$_2$R$^b$, wherein said C$_{1-6}$ alkyl is optionally substituted by OR$^a$;
each Cy$^1$ is independently selected from C$_{3-7}$ cycloalkyl optionally substituted by 1 or 2 substituents independently selected from OR$^{a1}$;
R$^1$ is C$_{1-6}$ alkyl;
R$^2$, R$^3$, and R$^4$ are each H;
each R$^a$ is independently selected from H, C$_{1-6}$ alkyl, C$_{1-6}$ haloalkyl, and 4-10 membered heterocycloalkyl-C$_{1-4}$ alkyl, wherein said C$_{1-6}$ alkyl of R$^a$ is optionally substituted with 1, 2, 3, 4, or 5 substituents independently selected from OR$^{a3}$, C(O)NR$^{c3}$R$^{d3}$, and NR$^{c3}$R$^{d3}$;
each R$^b$ is independently selected from C$_{1-6}$ alkyl;
each R$^c$ and R$^d$ is independently selected from H, C$_{1-6}$ alkyl, C$_{1-6}$ haloalkyl, and 4-10 membered heterocycloalkyl;
each R$^{a1}$ is independently selected from H and C$_{1-6}$ alkyl; and
each R$^{a3}$, R$^{c3}$, and R$^{d3}$ is independently selected from H and C$_{1-6}$ alkyl.

In some embodiments, the compound is selected from:
6-(1H-imidazol-1-yl)-4-(((1r,4r)-4-(2-methoxyethoxy)cyclohexyl)amino)-1-methylquinolin-2(1H)-one;
6-(1H-imidazol-1-yl)-1-methyl-4-(((1r,4r)-4-(oxetan-3-ylamino)cyclohexyl)amino)quinolin-2(1H)-one;
6-(1H-imidazol-1-yl)-4-(((1r,4r)-4-(2-methoxyethoxy)cyclohexyl)amino)-1-methyl-1,5-naphthyridin-2(1H)-one;
4-(((1r,4r)-4-(2-hydroxypropan-2-yl)cyclohexyl)amino)-6-(1H-imidazol-1-yl)-1-methyl-1,5-naphthyridin-2(1H)-one;
4-(((1r,4r)-4-(2-hydroxypropan-2-yl)cyclohexyl)amino)-6-(1H-imidazol-1-yl)-1-methyl-1,7-naphthyridin-2(1H)-one;
6-(1H-imidazol-1-yl)-4-(((1r,4r)-4-(2-methoxyethoxy)cyclohexyl)amino)-1-methyl-1,7-naphthyridin-2(1H)-one;
2-(1H-imidazol-1-yl)-8-(((1r,4r)-4-(2-methoxyethoxy)cyclohexyl)amino)-5-methylpyrido[3,2-d]pyrimidin-6(5H)-one;
8-(((1r,4r)-4-(2-hydroxypropan-2-yl)cyclohexyl)amino)-2-(1H-imidazol-1-yl)-5-methylpyrido[3,2-d]pyrimidin-6(5H)-one;
2-(1H-imidazol-1-yl)-5-methyl-8-((4-(trifluoromethyl)phenyl)amino)pyrido[3,2-d]pyrimidin-6(5H)-one;
2-(1H-imidazol-1-yl)-5-methyl-8-((6-(2-morpholinoethoxy)pyridin-3-yl)amino)pyrido[3,2-d]pyrimidin-6(5H)-one;
6-(1H-imidazol-1-yl)-1-methyl-4-(((1r,4r)-4-((2,2,2-trifluoroethyl)amino)cyclohexyl)amino)quinolin-2(1H)-one;
4-(((1r,4r)-4-(2-hydroxypropan-2-yl)cyclohexyl)amino)-6-(1H-imidazol-1-yl)-1-methylquinolin-2(1H)-one;
6-(1H-imidazol-1-yl)-1-methyl-4-(1-(methylsulfonyl)piperidin-4-yl)amino)quinolin-2(1H)-one;
2-(((1r,4r)-4-((6-(1H-imidazol-1-yl)-1-methyl-2-oxo-1,2-dihydroquinolin-4-yl)amino)cyclohexyl)oxy)-N,N-dimethylacetamide;
6-(1H-imidazol-1-yl)-1-methyl-4-((6-(2,2,2-trifluoroethoxy)pyridin-3-yl)amino)quinolin-2(1H)-one;
4-(((1r,4r)-4-((2,2-difluoropropyl)amino)cyclohexyl)amino)-6-(1H-imidazol-1-yl)-1-methylquinolin-2(1H)-one;
4-((6-(2-(dimethylamino)ethoxy)pyridin-3-yl)amino)-6-(1H-imidazol-1-yl)-1-methylquinolin-2(1H)-one;
6-(1H-imidazol-1-yl)-1-methyl-4-(((1r,4r)-4-(2-(pyrrolidin-1-yl)ethoxy)cyclohexyl)amino)quinolin-2(1H)-one;
8-(((1r,4r)-4-((2,2-difluoropropyl)amino)cyclohexyl)amino)-2-(1H-imidazol-1-yl)-5-methylpyrido[3,2-d]pyrimidin-6(5H)-one;
8-(1S,4r)-4-((S)-1-hydroxyethyl)cyclohexyl)amino)-2-(1H-imidazol-1-yl)-5-methylpyrido[3,2-d]pyrimidin-6(5H)-one;
2-(((1r,4r)-4-((2-(1H-imidazol-1-yl)-5-methyl-6-oxo-5,6-dihydropyrido[3,2-d]pyrimidin-8-yl)amino)cyclohexyl)oxy)-N,N-dimethylacetamide;
4-((2-(1H-imidazol-1-yl)-5-methyl-6-oxo-5,6-dihydropyrido[3,2-d]pyrimidin-8-yl)amino)benzonitrile;
2-(1H-imidazol-1-yl)-5-methyl-8-(((1r,4r)-4-((2,2,2-trifluoroethyl)amino)cyclohexyl)amino)pyrido[3,2-d]pyrimidin-6(5H)-one;
2-(1H-imidazol-1-yl)-8-(((1r,4r)-4-methoxycyclohexyl)amino)-5-methylpyrido[3,2-d]pyrimidin-6(5H)-one;
2-(1H-imidazol-1-yl)-5-methyl-8-(((6-(2-(pyrrolidin-1-yl)ethoxy)pyridin-3-yl)amino)pyrido[3,2-d]pyrimidin-6(5H)-one;
8-((4,4-difluorocyclohexyl)amino)-2-(1H-imidazol-1-yl)-5-methylpyrido[3,2-d]pyrimidin-6(5H)-one;
8-(((1r,4r)-4-(1-hydroxycyclopropyl)cyclohexyl)amino)-2-(1H-imidazol-1-yl)-5-methylpyrido[3,2-d]pyrimidin-6(5H)-one; and
8-(((1r,4r)-4-(2-methoxyethoxy)cyclohexyl)amino)-5-methyl-2-(thiazol-5-yl)pyrido[3,2-d]pyrimidin-6(5H)-one,
or a pharmaceutically acceptable salt of any of the aforementioned.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "C$_{1-6}$ alkyl" is specifically intended to individually disclose methyl, ethyl, C$_3$ alkyl, C$_4$ alkyl, C$_5$ alkyl, and C$_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "pyridinyl," "pyridyl," or "a pyridine ring" may refer to a pyridin-2-yl, pyridin-3-yl, or pyridin-4-yl ring.

The term "n-membered," where "n" is an integer, typically describes the number of ring-forming atoms in a moiety where the number of ring-forming atoms is "n". For example, piperidinyl is an example of a 6-membered heterocycloalkyl ring, pyrazolyl is an example of a 5-membered heteroaryl ring, pyridyl is an example of a 6-membered heteroaryl ring, and 1, 2, 3, 4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen group. It is to be understood that substitution at a given atom is limited by valency.

As used herein, the term "$C_{i-j}$," where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. In some embodiments, the alkyl group contains 1 to 7, 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, n-heptyl, and the like. In some embodiments, the alkyl group is methyl, ethyl, or propyl.

As used herein, the term "alkylene," employed alone or in combination with other terms, refers to a linking alkyl group.

As used herein, "alkenyl," employed alone or in combination with other terms, refers to an alkyl group having one or more carbon-carbon double bonds. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl," employed alone or in combination with other terms, refers to an alkyl group having one or more carbon-carbon triple bonds. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, "halo" or "halogen", employed alone or in combination with other terms, includes fluoro, chloro, bromo, and iodo. In some embodiments, halo is F or Cl.

As used herein, the term "haloalkyl," employed alone or in combination with other terms, refers to an alkyl group having up to the full valency of halogen atom substituents, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like.

As used herein, the term "alkoxy," employed alone or in combination with other terms, refers to a group of formula —O-alkyl. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "haloalkoxy," employed alone or in combination with other terms, refers to a group of formula —O-(haloalkyl). In some embodiments, the haloalkoxy group has 1 to 6 or 1 to 4 carbon atoms. An example haloalkoxy group is —$OCF_3$.

As used herein, "amino," employed alone or in combination with other terms, refers to $NH_2$.

As used herein, the term "alkylamino," employed alone or in combination with other terms, refers to a group of formula —NH(alkyl). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "dialkylamino," employed alone or in combination with other terms, refers to a group of formula —N(alkyl)$_2$. Example dialkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "cycloalkyl," employed alone or in combination with other terms, refers to a non-aromatic cyclic hydrocarbon including cyclized alkyl and alkenyl groups. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5]octane and the like). In some embodiments, the cycloalkyl group has 3 to 10 ring members, or 3 to 7 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "cycloalkylalkyl," employed alone or in combination with other terms, refers to a group of formula cycloalkyl-alkyl-. In some embodiments, the alkyl portion has 1 to 4, 1 to 3, 1 to 2, or 1 carbon atom(s). In some embodiments, the alkyl portion is methylene. In some embodiments, the cycloalkyl portion has 3 to 10 ring members or 3 to 7 ring members. In some embodiments, the cycloalkyl group is monocyclic or bicyclic. In some embodiments, the cycloalkyl portion is monocyclic. In some embodiments, the cycloalkyl portion is a $C_{3-7}$ monocyclic cycloalkyl group.

As used herein, the term "heterocycloalkyl," employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Where the heterocycloalkyl group includes a fused aromatic ring, the heterocycloalkyl group can be attached to the main structure though either the aromatic or non-aromatic ring. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-aza-spiro[4.5]decan-N-yl] and the like). In some embodiments, the heterocycloalkyl group has 3 to 10 ring-forming atoms, 4 to 10 ring-forming atoms, or about 3 to 8 ring forming atoms. In some embodiments, the heterocycloalkyl group has 2 to 20 carbon atoms, 2 to 15 carbon atoms, 2 to 10 carbon atoms, or about 2 to 8 carbon atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, tetrahydropyran ring, tetrahyropyridine, azetidine ring, or tetrahydrofuran ring.

As used herein, the term "heterocycloalkylalkyl," employed alone or in combination with other terms, refers to a group of formula heterocycloalkyl-alkyl-. In some embodiments, the alkyl portion has 1 to 4, 1 to 3, 1 to 2, or 1 carbon atom(s). In some embodiments, the alkyl portion is methylene. In some embodiments, the heterocycloalkyl portion has 3 to 10 ring members, 4 to 10 ring members, or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a $C_{2-7}$ monocyclic heterocycloalkyl group.

As used herein, the term "aryl," employed alone or in combination with other terms, refers to a monocyclic or polycyclic (e.g., a fused ring system) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl.

As used herein, the term "arylalkyl," employed alone or in combination with other terms, refers to a group of formula aryl-alkyl-. In some embodiments, the alkyl portion has 1 to 4, 1 to 3, 1 to 2, or 1 carbon atom(s). In some embodiments, the alkyl portion is methylene. In some embodiments, the aryl portion is phenyl. In some embodiments, the aryl group is a monocyclic or bicyclic group. In some embodiments, the arylalkyl group is benzyl.

As used herein, the term "heteroaryl," employed alone or in combination with other terms, refers to a monocyclic or polycyclic (e.g., a fused ring system) aromatic hydrocarbon moiety, having one or more heteroatom ring members independently selected from nitrogen, sulfur and oxygen. In some embodiments, the heteroaryl group is a monocyclic or a bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In some embodiments, the heteroaryl group has from 3 to 10 carbon atoms, from 3 to 8 carbon atoms, from 3 to 5 carbon atoms, from 1 to 5 carbon atoms, or from 5 to 10 carbon atoms. In some embodiments, the heteroaryl group contains 3 to 14, 4 to 12, 4 to 8, 9 to 10, or 5 to 6 ring-forming atoms. In some embodiments, the heteroaryl group has 1 to 4, 1 to 3, or 1 to 2 heteroatoms.

As used herein, the term "heteroarylalkyl," employed alone or in combination with other terms, refers to a group of formula heteroaryl-alkyl-. In some embodiments, the alkyl portion has 1 to 4, 1 to 3, 1 to 2, or 1 carbon atom(s). In some embodiments, the alkyl portion is methylene. In some embodiments, the heteroaryl portion is a monocyclic or bicyclic group having 1, 2, 3, or 4 heteroatoms independently selected from nitrogen, sulfur and oxygen. In some embodiments, the heteroaryl portion has 5 to 10 carbon atoms.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Geometric isomers of olefins, C=N double bonds, and the like can also be present in the compounds described herein, and all such stable isomers are contemplated in the present invention. Cis and trans geometric isomers of the compounds of the present invention may be isolated as a mixture of isomers or as separated isomeric forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution. Tautomeric forms can also include methyltropic tautomers, which result from the swapping of a single bond with an adjacent double bond together with the concomitant migration of a methyl group. Methyltropic tautomers can include, for example, 2-methyl-2H-pyrazolo[3,4-c]pyridine and 1-methyl-1H-pyrazolo[3,4-c]pyridine.

Compounds of the invention also include all isotopes of atoms occurring in the intermediates or final compounds. Isotopes include those atoms having the same atomic number but different mass numbers. For example, isotopes of hydrogen include tritium and deuterium. In some embodiments, the compounds of the invention include at least one deuterium atom.

The term, "compound," as used herein is meant to include all stereoisomers, geometric isomers, tautomers, and isotopes of the structures depicted, unless otherwise specified.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of a compound of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "RT", as used herein, are understood in the art, and refer generally to a temperature, e.g. a reaction temperature, that is about the temperature of the room in which the reaction is carried out, for example, a temperature from about 20° C. to about 30° C.

Compounds of Formula I can be prepared according to numerous preparatory routes known in the literature. Example synthetic methods for preparing compounds of the invention are provided in the Schemes below. Unless noted otherwise, all substituents are as defined herein.

Scheme 1

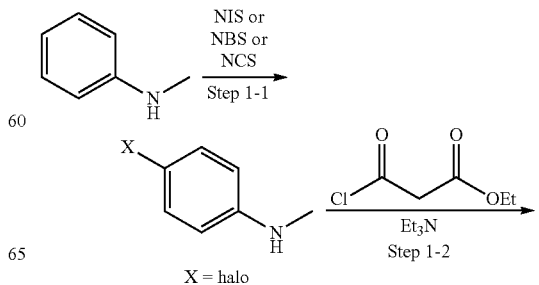

X = halo

-continued

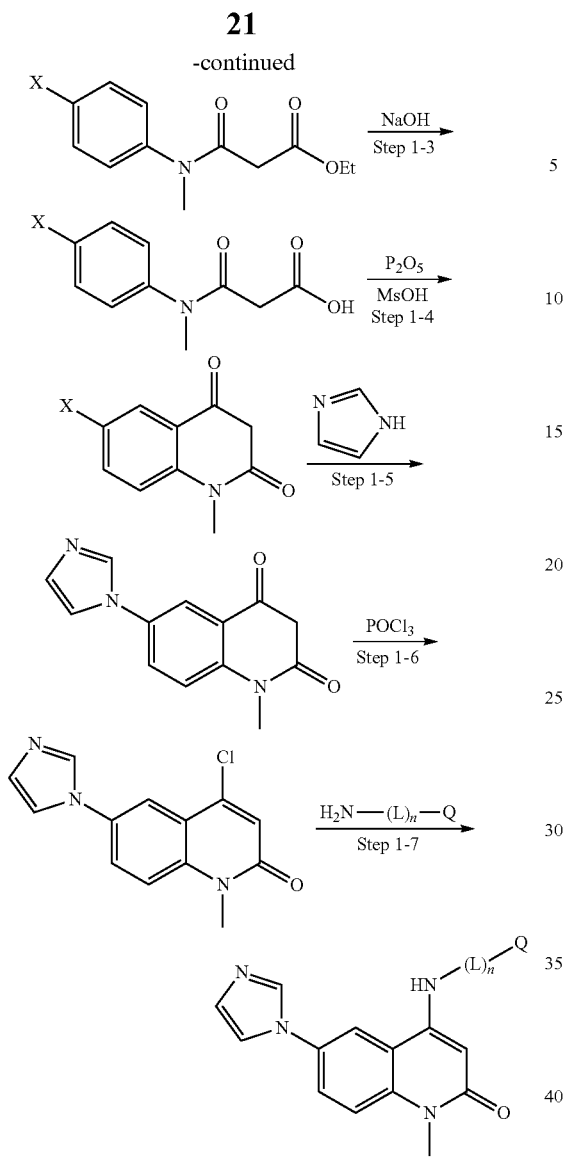

Scheme 2

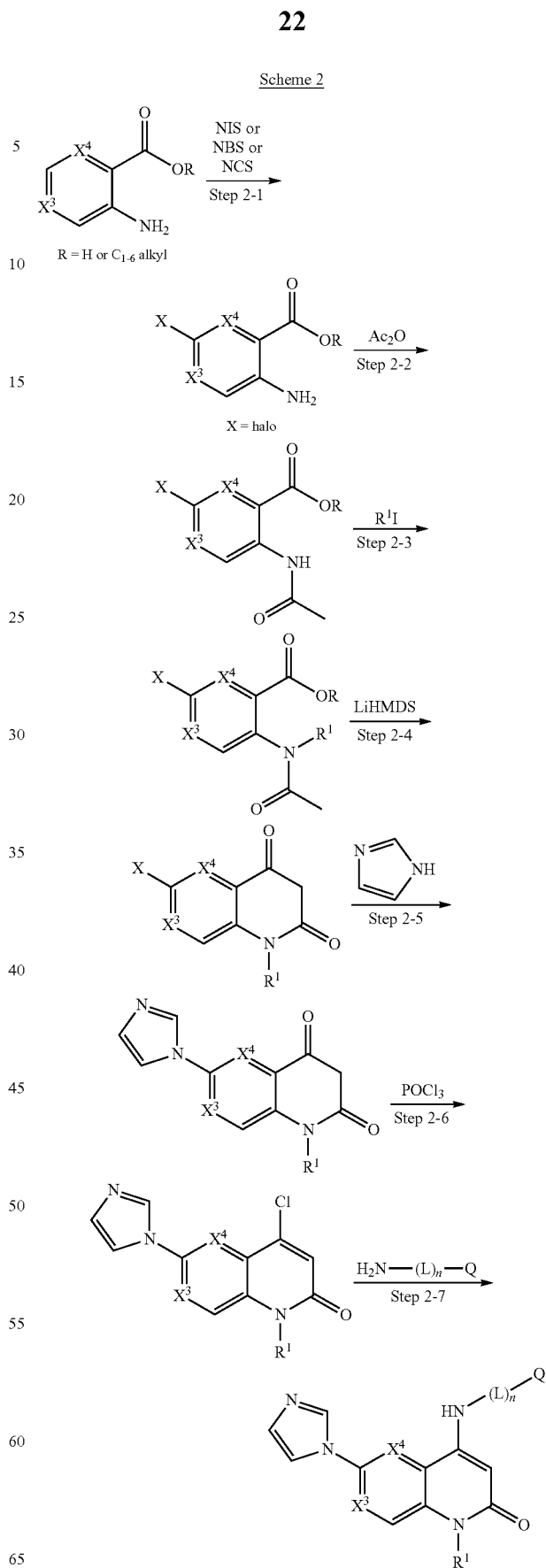

Scheme 1 shows the synthesis of analogs following a general route that utilizes well-established chemistry. Alkylated anilines can be treated with a reagent such as iodosuccinimide or any N-halo succinimide in a polar solvent such as DMF at room temperature to afford the para-halogenated aniline (step 1-1). The aniline can be acylated with a mono alkyl malonate and a base such as triethylamine in a solvent such as ethyl acetate (step 1-2). The resulting esters can be hydrolyzed by a base such as sodium hydroxide in the presence of water to give carboxylic acids (Step 1-3), which can then be cyclized under acidic conditions at elevated temperature (step 1-4) using phosphorus pentoxide. An imidazole ring can be introduced by treatment with imidazole in the presence of a base such as $K_2CO_3$, a catalyst such as CuI and a ligand such as L-proline in a polar solvent such as DMSO at elevated temperature (step 1-5). The dione can be converted to the chloroquinolinone with treatment of a reagent such as phosphoryl chloride (step 1-6). The resulting aryl chloride can be converted to desired analogs by treatment with amines $NH_2(L)_nQ$ and a Pd catalyst such as $Pd(OAc)_2$, a ligand such as BINAP, and a base such as t-BuONa in a non-polar solvent such as toluene at elevated temperature (step 1-7).

Scheme 2 shows an alternative route to the desired analogs. Heteroarylamino acids can be treated with a reagent such as iodosuccinimide or any N-halo succinimide in a polar solvent such as acetic acid at room temperature or elevated temperatures to afford the para-halogenated aniline (step 2-1). The aniline can be acylated by treatment with a reagent such as acetic anhydride and a base such as triethylamine in a solvent such as THF (step 2-2). The resulting amide can be alkylated with a reagent such as methyl iodide and base such as cesium carbonate in a polar solvent such as DMF at room temperature (step 2-3) then the ring cyclized with a strong base such as LiHMDS in a solvent such as THF (step 2-4). An imidazole ring can be introduced by treatment with imidazole in the presence of a base such as $K_2CO_3$, a catalyst such as CuI and a ligand such as L-proline in a polar solvent such as DMSO at elevated temperature (step 2-5). The dione can be converted to the chloroquinolinone with treatment of a reagent such as phosphoryl chloride (step 2-6). The resulting aryl chloride can be converted to desired analogs by treatment with amines $NH_2(L)_nQ$ and a Pd catalyst such as $Pd(OAc)_2$, a ligand such as BINAP, and a base such as t-BuONa in a non-polar solvent such as toluene at elevated temperature (step 2-7).

ods known to one skilled in the art (Step 3-1). These include, for example, coupling an aromatic tributylstannane in the presence of a Pd catalyst such as $Pd(dppf)Cl_2$ in a polar solvent such as DMF at elevated temperature. Alternatively, an imidazole ring can be introduced by treatment with imidazole in the presence of a base such as $K_2CO_3$, a catalyst such as CuI and a ligand such as L-proline in a polar solvent such as DMSO at elevated temperature. The bis-heterocycle can be converted to the dione via a 1 pot reaction by treating the aryl fluoride with N-methylacetamide and a strong base such as LiHMDS in a solvent such as THF (step 3-2). The dione can be converted to the chloroquinolinone with treatment of a reagent such as phosphoryl chloride (step 3-3). The resulting aryl chloride can be converted to desired analogs by treatment with amines $NH_2(L)_nQ$ and a Pd catalyst such as $Pd(OAc)_2$, a ligand such as BINAP, and a base such as $Cs_2CO_3$ in a non-polar solvent such as toluene at elevated temperature (step 3-4).

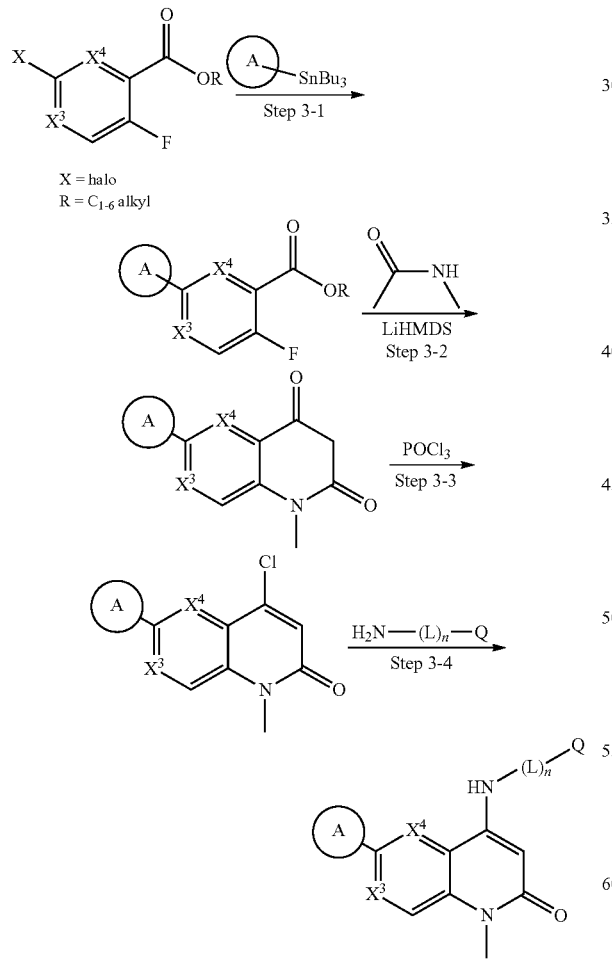

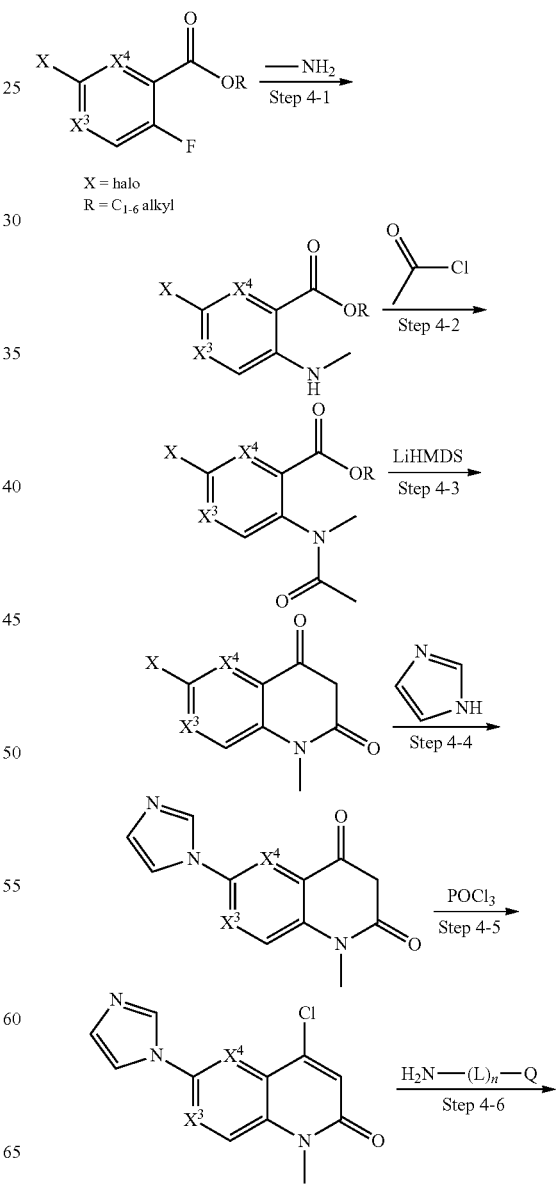

Scheme 3 shows another route to the desired analogs. Substituted haloaromatic esters can be coupled with a 5-membered heteroaromatic ring via several different meth-

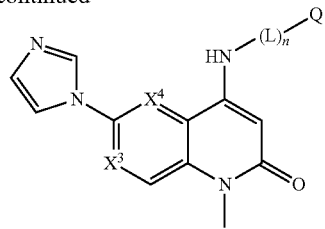

Scheme 4 shows an alternative route to the desired analogs. Halo-fluoroheteroaryl esters can be treated with a reagent such as methylamine and a base such as DIEA and in a solvent such as ACN at room temperature or elevated temperatures to afford methyl amine (step 4-1). The aniline can be acylated by treatment with a reagent such as acyl chloride and a base such as triethylamine in a solvent such as DCM (step 4-2). Cyclization can be accomplished with a strong base such as LiHMDS in a solvent such as THF (step 4-3). An imidazole ring can be introduced by treatment with imidazole in the presence of a base such as $K_2CO_3$, a catalyst such as CuI and a ligand such as L-proline in a polar solvent such as DMSO at elevated temperature (step 4-4). The dione can be converted to the chloroquinolinone by treatment of a reagent such as phosphoryl chloride (step 4-5). The resulting aryl chloride can be converted to desired analogs by treatment with amines $NH_2(L)_nQ$ and a Pd catalyst such as $Pd(OAc)_2$, a ligand such as BINAP, and a base such as t-BuONa in a non-polar solvent such as toluene at elevated temperature (step 4-6).

Methods of Use

Compounds of the invention can inhibit the activity of CD38. For example, the compounds of the invention can be used to inhibit activity or a function of CD38 in a cell or in an individual or patient in need of inhibition of the enzyme by administering an inhibiting amount of a compound of the invention to the cell, individual, or patient. As used herein, the term "in a cell" includes both inside the cell membrane and on the surface of the cell membrane.

Compounds of the invention, as CD38 inhibitors, can increase levels of $NAD^+$. Accordingly, the present invention is further directed to a method of increasing the level of $NAD^+$ in a sample or in a patient, comprising contacting the sample or administering to the patient a compound of Formula I, or a pharmaceutically acceptable salt thereof, wherein the increased level of $NAD^+$ is relative to the level of $NAD^+$ prior to the contacting or administering.

The compounds of the invention are useful in the treatment of various diseases associated with abnormal expression or activity of CD38. For example, the compounds of the invention are useful in the treatment of cancer. In some embodiments, the cancers are characterized in having abnormal expression or activity of CD38, for example, elevated expression or activity, compared with normal cells. In some embodiments, the cancers treatable according to the present invention include breast, central nervous system, endometrium, kidney, large intestine, lung, oesophagus, ovary, pancreas, prostate, stomach, head and neck (upper aerodigestive), urinary tract, colon, and others.

The compounds of the invention are useful in the treatment of tumors with exhausted T cells (for example, see Hashimoto M, Kamphorst A O, Im S J, et al. CD8 T Cell Exhaustion in Chronic Infection and Cancer: Opportunities for Interventions. *Annu Rev Med.* 2018; 69: 301-318. doi: 10.1146/annurev-med-012017-043208) and tumors defined as hot, altered, and cold immune tumors based on immunoscore (for example, see Galon J, Bruni D. Approaches to treat immune hot, altered and cold tumours with combination immunotherapies. *Nat Rev Drug Discov.* 2019; 18(3):197-218. doi:10.1038/s41573-018-0007-y).

In some embodiments, the cancers treatable according to the present invention include hematopoietic malignancies such as leukemia and lymphoma. Example lymphomas include Hodgkin's or non-Hodgkin's lymphoma, multiple myeloma, B-cell lymphoma (e.g., diffuse large B-cell lymphoma (DLBCL)), chronic lymphocytic lymphoma (CLL), T-cell lymphoma, hairy cell lymphoma, and Burkett's lymphoma. Example leukemias include acute lymphocytic leukemia (ALL), acute myelogenous leukemia (AML), chronic lymphocytic leukemia (CLL), and chronic myelogenous leukemia (CML).

In some embodiments, the cancer treatable by administration of the compounds of the invention is lung cancer.

In some embodiments, the cancer treatable by administration of the compounds of the invention is melanoma.

In some embodiments, the cancer treatable by administration of the compounds of the invention is colon cancer.

Other cancers treatable by the administration of the compounds of the invention include checkpoint therapy-treated cancers, checkpoint therapy-treated resistant cancers, adenosine-dependent tumors, Treg-infiltrated tumors, and MD SC-infiltrated tumors.

Other cancers treatable by the administration of the compounds of the invention include bladder cancer, bone cancer, glioma, breast cancer, cervical cancer, colon cancer, endometrial cancer, epithelial cancer, esophageal cancer, Ewing's sarcoma, pancreatic cancer, gallbladder cancer, gastric cancer, gastrointestinal tumors, glioma, head and neck cancer (upper aerodigestive cancer), intestinal cancers, Kaposi's sarcoma, kidney cancer, laryngeal cancer, liver cancer (e.g., hepatocellular carcinoma), lung cancer (e.g., non-small cell lung cancer, adenocarcinoma), melanoma, prostate cancer, rectal cancer, renal clear cell carcinoma, skin cancer, stomach cancer, testicular cancer, thyroid cancer, and uterine cancer.

In some embodiments, the cancer treatable by administration of the compounds of the invention is multiple myeloma, diffuse large B-cell lymphoma (DLBCL), hepatocellular carcinoma, bladder cancer, esophageal cancer, head and neck cancer (upper aerodigestive cancer), kidney cancer, prostate cancer, rectal cancer, stomach cancer, thyroid cancer, uterine cancer, and breast cancer.

Other cancers treatable by the administration of the compounds of the invention include checkpoint therapy-treated cancers, checkpoint therapy-treated resistant cancers, adenosine-dependent tumors, Treg-infiltrated tumors, and MDSC-infiltrated tumors.

The compounds of the invention can also be used to treat the following diseases or conditions: HIV/AIDS, adoptive T cell therapy, acute lung injury, acute respiratory distress syndrome (ARDS), hyperphosphatemia, alcohol intolerance, lupus, rheumatoid arthritis ataxia-telangiectasia, sleep disorders, epilepsy, exercise intolerance, hypertension, hypoxic pulmonary vasoconstriction, hansen's disease, tuberculosis, leishmaniasis, cardiac hypertrophy, congestive heart failure (CHF), muscular dystrophy, stroke, organ reperfusion injury, idiopathic pulmonary fibrosis, pancreatitis, cystic fibrosis, asthma, chronic obstructive pulmonary disease (COPD), Irritable Bowel Syndrome (IBS), colitis, gout, obesity, sarcopenic obesity, Metabolic Syndrome, end stage renal disease, dyslipidemia, hearing loss, liver disease, steatosis, nonalcoholic steatohepatitis (NASH/NAFLD), asthma, allergic airway disease, Alzheimer's disease, multiple sclerosis, neurodegenration, neurological diseases, systemic sclerosis, multi-organ fibrosis, age related ailments, neurocognitive disorders, optic neuropathy, postmenopausal osteoporosis, bipolar disorder, schizophrenia, Huntington's disease, diabetes, Hartnup disease, skin hyperpigmentation, diabetic neuropathy, radiation exposure, UV skin damage, psoriasis, periodontal disease, chronic lymphocytic leukemia, amyelotrophic lateral sclerosis, Parkinson's disease, Leber's hereditary amaurosisinsulin resistance, and type I diabetes.

The CD38 inhibitors of the invention may also have therapeutic utility in CD38-related disorders in disease areas such as cardiology, virology, neurodegeneration, inflammation, and pain, particularly where the diseases are characterized by overexpression or increased activity of CD38.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" CD38 or "contacting" a cell with a compound of the invention includes the administration of a compound of the present invention to an individual or patient, such as a human, having CD38, as well as, for example, introducing a compound of the invention into a sample containing a cellular or purified preparation containing CD38.

As used herein, the term "individual" or "patient," used interchangeably, refers to mammals, and particularly humans. The individual or patient can be in need of treatment.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease in an individual who is experiencing or displaying the pathology or symptomatology of the disease (i.e., arresting further development of the pathology and/or symptomatology), or 2) ameliorating the disease in an individual who is experiencing or displaying the pathology or symptomatology of the disease (i.e., reversing the pathology and/or symptomatology).

As used herein the term "preventing" or "prevention" refers to preventing the disease in an individual who may be predisposed to the disease but does not yet experience or display the pathology or symptomatology of the disease. In some embodiments, the invention is directed to a method of preventing a disease in a patient, by administering to the patient a therapeutically effective amount of a compound of Formula I, or a pharmaceutically acceptable salt thereof.

Combination Therapy

One or more additional pharmaceutical agents or treatment methods such as, for example, chemotherapeutics or other anti-cancer agents, immune enhancers, immunosuppressants, immunotherapies, radiation, anti-tumor and anti-viral vaccines, cytokine therapy (e.g., IL2, GM-CSF, etc.), and/or kinase (tyrosine or serine/threonine), epigenetic or signal transduction inhibitors can be used in combination with the compounds of the present invention. The agents can be combined with the present compounds in a single dosage form, or the agents can be administered simultaneously or sequentially as separate dosage forms.

Suitable agents for use in combination with the compounds of the present invention for the treatment of cancer include chemotherapeutic agents, targeted cancer therapies, immunotherapies or radiation therapy. Compounds of this invention may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present invention. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Suitable agents for use in combination with the compounds of the present invention for the treatment of cancer further include agents that target adenosine signaling like A2aR and A2bR, inhibitors and nodes of adenosine generating pathway like CD39, CD73, and ENPP1 inhibitors, and agents that target generation of immunosuppressive amino acids and their products like IDO inhibitors and AHR inhibitors.

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other anti-cancer agent(s) include antibody therapeutics to checkpoint or costimulatory molecules such as CTLA-4, PD-1, PD-L1 or 4-1BB, respectively, or antibodies to cytokines TGF-β, etc.). Exemplary cancer immunotherapy antibodies include pembrolizumab, ipilimumab, nivolumab, atezolizumab and durvalumab. Additional anti-cancer agent(s) include antibody therapeutics directed to surface molecules of hematological cancers such as ofatumumab, rituximab and alemtuzumab.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

Pharmaceutical Formulations and Dosage Forms When employed as pharmaceuticals, the compounds of the invention can be administered in the form of pharmaceutical compositions. A pharmaceutical composition refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be oral, topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, or parenteral.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The compositions can be formulated in a unit dosage form. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1

μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, anti-cancer agents, vaccines, antibodies, immune enhancers, immune suppressants, anti-inflammatory agents and the like.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of CD38 according to one or more of the assays provided herein.

Equipment: $^1$H NMR Spectra were recorded at 300 or 400 MHz using a Bruker AVANCE 300 MHz/400 MHz spectrometer. NMR interpretation was performed using Bruker Topspin software to assign chemical shift and multiplicity. In cases where two adjacent peaks of equal or unequal height were observed, these two peaks may be labeled as either a multiplet or as a doublet. In the case of a doublet, a coupling constant using this software may be assigned. In any given example, one or more protons may not be observed due to obscurity by water and/or solvent peaks. LCMS equipment and conditions are as follows:

1. LC (Basic condition): Shimadzu LC-20ADXR, Binary Pump, Diode Array Detector. Column: Poroshell HPH-C18 50*3.0 mm, 2.7 μm. Mobile phase: A: Water/6.5 mM NH$_4$HCO$_3$ pH=10; B: Acetonitrile. Flow Rate: 1.2 mL/min at 40° C. Detector: 190-400 nm. Gradient stop time 3.0 min. Timetable:

| T (min) | A(%) | B(%) |
|---|---|---|
| 0.01 | 90 | 10 |
| 2.00 | 5 | 95 |
| 2.70 | 5 | 95 |
| 2.75 | 90 | 10 |

2. LC (Basic condition): Shimadzu LC-20ADXR, Binary Pump, Diode Array Detector. Column: Shim-pack scepter C18 33*3.0 mm, 3.0 μm. Mobile phase: A: Water/5 mM NH$_4$HCO$_3$; B: Acetonitrile. Flow Rate: 1.5 mL/min at 40° C. Detector: 190-400 nm. Gradient stop time 2.0 min. Timetable:

| T(min) | A(%) | B(%) |
|---|---|---|
| 0.01 | 90 | 10 |
| 1.20 | 5 | 95 |
| 1.80 | 5 | 95 |
| 1.82 | 90 | 10 |

3. LC (acidic condition): Shimadzu LC-20ADXR, Binary Pump, Diode Array Detector. Column: Halo C18, 30*3.0 mm, 2.0 μm. Mobile phase: A: Water/0.05% TFA, B: Acetonitrile/0.05% TFA. Flow Rate: 1.5 mL/min at 40° C. Detector: 190-400 nm. Gradient stop time, 2.0 min. Timetable:

| T (min) | A(%) | B(%) |
|---|---|---|
| 0.01 | 90 | 5 |
| 1.20 | 5 | 100 |
| 1.80 | 5 | 100 |
| 1.82 | 90 | 5 |

4. LC (Acidic condition): Shimadzu LC-30AD, Binary Pump, Diode Array Detector. Column: Halo C18, 30*3.0 mm, 2.0 μm. Mobile Phase A: Water/0.1% FA Mobile Phase B: Acetonitrile/0.1% FA. Flow Rate: 1.5 mL/min at 40° C. Detector: 190-400 nm. Gradient stop time 3.0 min Timetable:

| T (min) | A(%) | B(%) |
|---|---|---|
| 0.01 | 90 | 5 |
| 1.20 | 5 | 100 |
| 1.80 | 5 | 100 |
| 1.82 | 90 | 5 |

5. The MS detector is configured with electrospray ionization as ionizable source; Acquisition mode: Scan; Nebulizing Gas Flow: 1.5 L/min; Drying Gas Flow: 15 L/min; Detector Voltage: 0.95-1.25 kv; DL Temperature: 250° C.; Heat Block Temperature: 250° C.; Scan Range: 90.00-900.00 m/z.

6. Sample preparation: samples were dissolved in ACN or methanol at 1~10 mg/mL, then filtered through a 0.22 μm filter membrane. Injection volume: 1~3 μL.

Definitions: ACN (acetonitrile); Ac$_2$O (acetic anhydride); AcOH (acetic acid); BINAP (2,2'-bis(diphenylphosphino)-1,1'-binaphthyl); Cs$_2$CO$_3$ (cesium carbonate); CuI (copper iodide); DCM (dichloromethane); DIEA (N,N-diisopropylethylamine); DMF (N,N-dimethylformamide); DMAP (4-dimethyl aminopyridine); DMSO (dimethylsulfoxide); DMSO-d$_6$ (deuterated dimethylsulfoxide); eq (equivalents); Et$_3$N (triethylamine); EtOAc (ethyl acetate); EtOH (ethanol); g (gram); h (hour); $^1$H NMR (proton nuclear magnetic resonance); HCl (hydrochloric acid); H$_2$O (water); Hz (hertz); K$_2$CO$_3$ (potassium carbonate); L (liter); LCMS (liquid chromatography-mass spectrometry); LiHMDS (lithium bis(trimethylsilyl)amide); M (molar); MeI (methyl iodide); MeOH (methanol); mg (milligrams); MHz (megahertz); mL (milliliters), mmol (millimoles); NaBH$_3$CN (Sodium cyanoborohydride); Na$_2$CO$_3$ (sodium carbonate); NaH (sodium hydride); NaHCO$_3$ (sodium bicarbonate); NaOH (sodium hydroxide); Na$_2$SO$_4$ (sodium sulfate); NIS (N-iodosuccinimide); NMP (N-methyl-2-pyrrolidone); P$_2$O$_5$ (phosphorus pentoxide); Pd/C (palladium on carbon); Pd(dppf)Cl$_2$ ([1,1'-bis(diphenylphosphino)ferrocene]dichloropalladium(II), complex with dichloromethane); Pd(OAc)$_2$ (palladium(II) acetate); PE (petroleum ether); prep-HPLC (preparative high-performance liquid chromatography); RT (room temperature); t-BuOK (potassium tert-butoxide); t-BuONa (sodium tert-butoxide); TEA (triethylamine); THF (tetrahydrofuran); Ti(Oi-Pr)$_4$ (titanium isopropoxide); TFA (trifluoroacetic acid).

Int-B1: (1r,4r)-4-(2-Methoxyethoxy)cyclohexan-1-amine

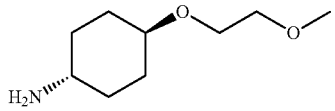

Step 1: (1r,4r)-4-(Dibenzylamino)cyclohexan-1-ol

A mixture of (1r,4r)-4-aminocyclohexan-1-ol (30.0 g, 260.5 mmol, 1.0 eq), benzyl bromide (133 g, 777.6 mmol, 3 eq), and $K_2CO_3$ (72.0 g, 520.9 mmol, 2 eq) in ACN (300 mL) was stirred for 2 h at 75° C. The reaction was quenched with water. The solids were collected by filtration to afford the title compound (65 g, 85%) as a white solid. LCMS: $[M+H]^+$ 296.2.

Step 2: (1r,4r)-N,N-Dibenzyl-4-(2-methoxyethoxy)cyclohexan-1-amine

A mixture of (1r,4r)-4-(dibenzylamino)cyclohexan-1-ol (59 g, 199.7 mmol, 1 eq), 1-bromo-2-methoxyethane (82.6 g, 594.3 mmol, 3 eq), and t-BuOK (33.6 g, 299.2 mmol, 1.5 eq) in DCM (1 L) was stirred for 4 h at RT. The reaction was quenched with water and extracted with 3×500 mL of DCM. The organic layers were combined, dried over sodium sulfate and concentrated. The crude product was purified by silica gel chromatography eluting with EtOAc/PE (5:95) to afford the title compound (48 g, 68%) as red oil. LCMS: $[M+H]^+$ 354.2.

Step 3: (1r,4r)-4-(2-Methoxyethoxy)cyclohexan-1-amine

Under hydrogen, a mixture of (1r,4r)-N,N-dibenzyl-4-(2-methoxyethoxy)cyclohexan-1-amine (60.0 g, 169.7 mmol, 1 eq) and $Pd(OH)_2$ on carbon (10.0 g, 71.2 mmol, 0.42 eq) in EtOH (600 mL) was stirred for 14 h at RT. The solids were filtered out. The filtrate was concentrated under vacuum to afford the title compound (27 g, 92%) as a yellow oil. LCMS: $[M+H]^+$ 174.1.

Example 1: 6-(1H-imidazol-1-yl)-4-(((1r,4r)-4-(2-methoxyethoxy)cyclohexyl)amino)-1-methylquinolin-2(1H)-one

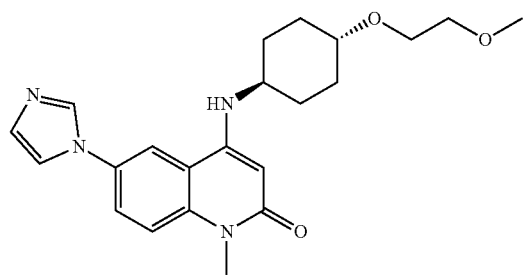 [SMILES: COCCO[C@H]1CC[C@H](Nc2cc(=O)n(C)c3ccc(-n4ccnc4)cc23)CC1]

Step 1: 4-iodo-N-methylaniline

A solution of N-methylaniline (23.0 g, 215 mmol, 1 eq) and NIS (48.3 g, 215 mmol, 1 eq) in DMF (240 mL) was stirred for 1 h at RT. The reaction was then quenched with water (500 mL.) The resulting solution was extracted with EtOAc (3×600 mL.) The organic layers were combined, washed with brine and concentrated to afford the title compound (41.5 g, 83%) as a black oil. LCMS: $[M+H]^+$ 234.00.

Step 2: ethyl 3-((4-iodophenyl)(methyl)amino)-3-oxopropanoate

A solution of 4-iodo-N-methylaniline (41.0 g, 176 mmol, 1 eq), $Et_3N$ (23.1 g, 229 mmol, 1.3 eq), and ethyl 3-chloro-3-oxopropanoate (39.7 g, 264 mmol, 1.5 eq) in EtOAc (500 mL) was stirred for 2 h at RT. The resulting solution was washed with $H_2O$ (3×500 mL.) The organic layer was concentrated and the residue purified by silica gel chromatography eluting with EtOAc/PE (1/9) to afford the title compound (50 g, 82%) as a yellow oil. LCMS: $[M+H]^+$ 348.05.

Step 3: 3-((4-iodophenyl)(methyl)amino)-3-oxopropanoic acid

A solution of NaOH (23.0 g, 576 mmol, 5.0 eq) in $H_2O$ (50 mL) was added to the solution of ethyl 3-((4-iodophenyl)(methyl)amino)-3-oxopropanoate (40.0 g, 115 mmol, 1 eq) in MeOH (150 mL) at 0° C. The resulting solution was stirred for 2 h at RT. The MeOH was removed by concentration then the pH value of the solution was adjusted to 4 with concentrated HCl. The solids were collected by filtration to afford the title compound (20 g, 54%) as a black solid. LCMS: $[M+H]^+$ 319.95.

Step 4: 6-iodo-1-methylquinohne-2,4(1H,3H)-dione

A solution of 3-((4-iodophenyl)(methyl)amino)-3-oxopropanoic acid (11.6 g, 36 mmol, 1.0 eq) and $P_2O_5$ (10.3 g, 72 mmol, 2.0 eq) in methanesulfonic acid (100 mL) was stirred for 5 h at 100° C. After completion, the reaction was quenched with water. The insoluble solids were collected by filtration to afford title compound (9.87 g, 91%) as a black solid. LCMS: $[M+H]^+$ 301.15.

Step 5: 6-(1H-imidazol-1-yl)-1-methylquinohne-2,4(1H,3H)-dione

A solution of 6-iodo-1-methylquinoline-2,4(1H,3H)-dione (2.00 g, 6.64 mmol, 1.0 eq), 1H-imidazole (3.62 g, 53.1 mmol, 8 eq), $K_2CO_3$ (1.84 g, 13.3 mmol, 2 eq), CuI (1.27 g, 6.64 mmol, 1.0 eq) and L-proline (382 mg, 3.32 mmol, 0.50 eq) in DMSO (25 ml) was stirred for 1.5 h at 120° C. The reaction was concentrated then the crude product was purified by reverse phase column eluting with $H_2O$/ACN to afford the title compound (800 mg, 50%) as a green solid. LCMS: $[M+H]^+$ 242.25

Step 6: 4-chloro-6-(1H-imidazol-1-yl)-1-methylquinohn-2(1H)-one

A solution of 6-(1H-imidazol-1-yl)-1-methylquinoline-2,4(1H,3H)-dione (5.5 g, 22.8 mmol, 1.0 eq) in phosphoryl trichloride (40 mL) was stirred for 2 h at 120° C. The resulting mixture was concentrated to remove most of phosphoryl trichloride. The crude product was dissolved in 100 mL of DCM. The pH value of the solution was adjusted to 8 with saturated aqueous $Na_2CO_3$. The solids were filtered out and the filtrate was extracted with DCM (3×500 mL), the organic layers were combined and concentrated under vacuum to afford the title compound (3.4 g, 57%) as a green solid. LCMS: [M+H]+ 260.15.

Step 7: 6-(1H-imidazol-1-yl)-4-(((1r,4r)-4-(2-methoxyethoxy)cyclohexyl)amino)-1-methylquinolin-2(1H)-one Under an atmosphere of nitrogen, a solution of 4-chloro-6-(1H-imidazol-1-yl)-1-methylquinolin-2(1H)-one (200 mg, 0.77 mmol, 1.0 eq), (1r,4r)-4-(2-methoxyethoxy)cyclohexan-1-amine (Int-B1, 200 mg, 1.16 mmol, 1.5 eq), Pd(OAc)$_2$ (17 mg, 0.077 mmol, 0.10 eq), BINAP (48 mg, 0.077 mmol, 0.10 eq), and t-BuONa (148 mg, 1.54 mmol, 2.0 eq) in toluene (5 mL) was stirred for 3 h at 60° C. The reaction was then concentrated under vacuum. The crude product was purified by reverse phase column eluting with H$_2$O/ACN (2/1) to afford the title compound (64.7 mg, 21%) as a white solid. LCMS: [M+H]+ 397.20. $^1$H NMR (300 MHz, DMSO-d6) δ 8.26 (d, J=0.9 Hz, 1H), 8.25 (s, 1H), 7.84 (dd, J=2.4, 9.0 Hz, 1H), 7.78 (t, J=1.5, 1.2 Hz, 1H), 7.53 (d, J=9.3 Hz, 1H), 7.14 (s, 1H), 6.55 (d, J=7.2 Hz, 1H), 5.57 (s, 1H), 3.60-3.51 (m, 1H), 3.50 (s, 3H), 3.50-3.43 (m, 3H), 3.32-3.29 (m, 2H), 3.20 (s, 3H), 2.13-2.03 (m, 4H), 1.50-1.20 (m, 4H).

Example 2: 6-(1H-imidazol-1-yl)-1-methyl-4-(((1r,4r)-4-(oxetan-3-ylamino)cyclohexyl)amino)quinolin-2(1H)-one

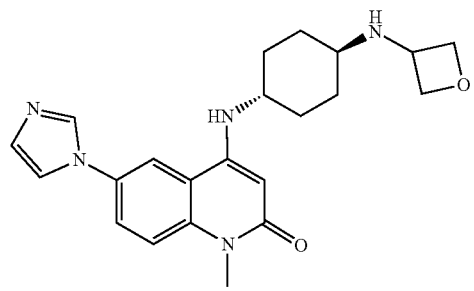 [SMILES: Cn1c(=O)cc(N[C@H]2CC[C@H](NC3COC3)CC2)c2cc(-n3ccnc3)ccc21]

Step 1: tert-butyl ((1r,4r)-4-((6-(1H-imidazol-1-yl)-1-methyl-2-oxo-1,2-dihydroquinolin-4-yl)amino)cyclohexyl)carbamate Under an atmosphere of nitrogen, a solution of 4-chloro-6-(1H-imidazol-1-yl)-1-methylquinolin-2(1H)-one (300 mg, 1.16 mmol, 1.0 eq), tert-butyl ((1r,4r)-4-aminocyclohexyl)carbamate (371 mg, 1.73 mmol, 1.5 eq), Pd(OAc)$_2$ (25.9 mg, 0.12 mmol, 0.10 equiv), BINAP (71.9 mg, 0.12 mmol, 0.10 eq), and t-BuONa (222 mg, 2.31 mmol, 2.0 eq) in toluene (6 mL) was stirred for 3 h at 75° C. The resulting solution was concentrated and purified by reverse phase column eluting with H$_2$O/ACN (1/1) to afford the title compound (296 mg, 59%) as light yellow solid. LCMS: [M+H]+ 437.25

Step 2: 4-(((1r,4r)-4-aminocyclohexyl)amino)-6-(1H-imidazol-1-yl)-1-methylquinoln-2(1H)-one di-hydrochloride A solution of tert-butyl ((1r,4r)-4-((6-(1H-imidazol-1-yl)-1-methyl-2-oxo-1,2-dihydroquinolin-4-yl)amino)cyclohexyl)carbamate (276 mg, 0.63 mmol, 1.0 eq) in HCl/1,4-dioxane (10 mL, 4M) was stirred for 1 h at RT. The reaction was then concentrated to remove most of solvent. The solids were collected by filtration to afford the crude title compound (261 mg) as white solid. LCMS: [M+H]+ 338.15.

Step 3: 6-(1H-imidazol-1-yl)-1-methyl-4-(((1r,4r)-4-(oxetan-3-ylamino)cyclohexyl)amino)quinolin-2(1H)-one A solution of 4-(((1r,4r)-4-aminocyclohexyl)amino)-6-(1H-imidazol-1-yl)-1-methylquinolin-2(1H)-one (130 mg, 0.39 mmol, 1.0 eq), oxetan-3-one (83.3 mg, 1.16 mmol, 3.0 eq), AcOH (23.1 mg, 0.39 mmol, 1.0 eq), and Ti(Oi-Pr)$_4$ (109.5 mg, 0.39 mmol, 1.0 eq) in EtOH (5 mL) was stirred for 3 h at 60° C. Then NaBH$_3$CN (36.3 mg, 0.58 mmol, 1.5 equiv) was added and the resulting solution was stirred for 1 h at 80° C. After completion, the reaction was concentrated under vacuum. The crude product was purified by reverse phase column eluting with H$_2$O/ACN (1/1) to afford the title compound (14 mg, 9.2%) as a white solid. LCMS: [M+H]+ 394.25. $^1$H NMR (300 MHz, DMSO-d6) δ 8.29 (s, 1H), 8.26 (d, J=4.8 Hz, 1H), 7.85 (d, J=2.4 Hz, 1H), 7.83 (s, 1H), 7.53 (d, J=9.0 Hz, 1H), 7.14 (d, J=0.9 Hz, 1H), 6.56 (d, J=7.2 Hz, 1H), 5.52 (s, 1H), 4.7-4.60 (m, 2H), 4.33-4.20 (m, 2H), 4.02-3.85 (m, 1H), 3.52 (s, 3H), 2.75-2.62 (m, 1H), 2.46-2.30 (m, 2H), 2.05-1.92 (m, 2H), 1.83-1.70 (m, 2H), 1.50-1.10 (m, 4H).

Example 3: 6-(1H-imidazol-1-yl)-4-(((1r,4r)-4-(2-methoxyethoxy)cyclohexyl)amino)-1-methyl-1,5-naphthyridin-2(1H)-one

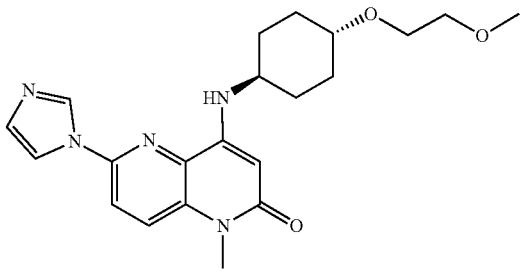 [SMILES: COCCO[C@H]1CC[C@H](Nc2cc(=O)n(C)c3ccc(-n4ccnc4)nc23)CC1]

Step 1: ethyl 3-amino-6-iodopicolinate

A solution of ethyl 3-aminopicolinate (10 g, 60.2 mmol, 1.0 eq) and NIS (14.2 g, 63.2 mmol, 1.05 eq) in acetic acid (35 mL) was stirred for 3 hours at room temperature, then heated at 50° C. for 12 hours. After completion, the reaction was concentrated then diluted with 500 mL of water. The solids were collected by filtration to afford the title compound (14.84 g, 84%) as a brown solid. LCMS: [M+H]+ 292.15.

Step 2: ethyl 3-acetamido-6-iodopicolinate

A solution of ethyl 3-amino-6-iodopicolinate (7008 mg, 24 mmol, 1.0 eq), Ac$_2$O (9798 mg, 96 mmol, 4.0 eq), TEA (4856 mg, 48 mmol, 2.0 eq), and DMAP (2931 mg, 24 mmol, 1.0 eq) in THF (30 mL) was stirred for 3 h at 75° C. After completion, the solids were filtered out. The filtrate was diluted with 100 mL of water and extracted with ethyl acetate (3×100 mL). The organic layers were combined and concentrated. The crude product was purified by silica gel chromatography eluting with EtOAc/PE (3/7) to afford the title compound (4300 mg, 53%) as a light yellow solid. LCMS: [M+H]$^+$ 335.15.

Step 3: ethyl 6-iodo-3-(N-methylacetamido)picolinate

A solution of ethyl 3-acetamido-6-iodopicolinate (4250 mg, 12.7 mmol, 1.0 eq), iodomethane (2708 mg, 19.1 mmol, 1.5 eq), and $Cs_2CO_3$ (6216 mg, 19.1 mmol, 1.5 eq) in DMF (15 mL) was stirred for 1 h at RT. The resulting solution was quenched with water (250 mL) and extracted with ethyl acetate (3×250 mL). The organic layers were combined, dried over $Na_2SO_4$, filtered and concentrated under reduced pressure to afford the title compound (4.00 g, 90%) as a yellow oil. LCMS: [M+H]$^+$ 349.15.

Step 4: 6-iodo-1-methyl-1,5-naphthyridine-2,4(1H,3H)-dione

Under an atmosphere of nitrogen, to a solution of ethyl 6-iodo-3-(N-methylacetamido)picolinate (3900 mg, 11.2 mmol, 1.0 eq) in THF (10 ml) was added LiHMDS in THF (13 mL, 1M, 1.2 eq) at 0° C. The reaction was stirred for 0.5 h at RT. After completion, the reaction was quenched with water (200 mL) and concentrated under reduced pressure to remove THF. The solids were collected by filtration to afford title compound (2.34 g, 70%) as a white solid. LCMS: [M+H]$^+$ 303.15.

Step 5: 6-(1H-imidazol-1-yl)-1-methyl-1,5-naphthyridine-2,4(1H,3H)-dione

Under an atmosphere of nitrogen, a solution of 6-iodo-1-methyl-1,5-naphthyridine-2,4(1H,3H)-dione (1000 mg, 3.31 mmol, 1.0 eq), 1H-imidazole (1803 mg, 26.5 mmol, 8.0 eq), $K_2CO_3$ (915 mg, 6.62 mmol, 2.0 eq), CuI (631 mg, 3.31 mmol, 1.0 eq), and L-proline (191 mg, 1.66 mmol, 0.50 eq) in DMSO (6 mL) was stirred for 3 h at 120° C. The solids were then filtered out and the filtrate was concentrated under reduced pressure. The crude product was purified by silica gel chromatography eluting with MeOH/DCM (17/83) to afford the title compound (617 mg, 77%) as a brown solid. LCMS: [M+H]$^+$ 243.15

Step 6: 4-chloro-6-(1H-imidazol-1-yl)-1-methyl-1,5-naphthyridin-2(1H)-one

A solution of 6-(1H-imidazol-1-yl)-1-methyl-1,5-naphthyridine-2,4(1H,3H)-dione (563.0 mg, 2.32 mmol, 1.0 eq) in phosphoryl trichloride (8.0 mL) was stirred for 2 h at 95° C. The reaction was concentrated to remove most of phosphoryl trichloride. The residue was dissolved in water at 0° C. The pH value of the solution was adjusted to 8 with saturated aqueous $Na_2CO_3$. The solids were collected by filtration to afford the title compound (287 mg, 47%) as brown solid. LCMS: [M+H]$^+$ 261.25

Step 7: 6-(1H-imidazol-1-yl)-4-(((1r,4r)-4-(2-methoxyethoxy)cyclohexyl)amino)-1-methyl-1,5-naphthyridin-2(1H)-one Under an atmosphere of nitrogen, a solution of 4-chloro-6-(1H-imidazol-1-yl)-1-methyl-1,5-naphthyridin-2(1H)-one (236 mg, 0.91 mmol, 1.0 eq), 2-((1r,4r)-4-aminocyclohexyl)propan-2-ol (235 mg, 1.36 mmol, 1.5 eq), Pd(OAc)$_2$ (20.3 mg, 0.091 mmol, 0.10 eq), BINAP (56.4 mg, 0.091 mmol, 0.10 eq), and t-BuONa (174.0 mg, 1.81 mmol, 2.0 eq) in toluene (5 mL) was stirred for 3 h at 75° C. The reaction was concentrated under vacuum and purified by reverse phase chromatography eluting with H$_2$O/ACN (7/3) to afford the title compound (31.1 mg, 8.6%) as light yellow solid. LCMS: [M+H]$^+$ 398.25.
$^1$H NMR (400 MHz, DMSO-d6) δ 8.89 (s, 1H), 8.25 (t, J=1.2, 1.2 Hz, 1H), 8.11-8.01 (dd, J=1.2, 0.9 Hz, 2H), 7.14 (s, 1H), 6.71 (d, J=4.8 Hz, 1H), 5.71 (s, 1H), 3.50-3.42 (m, 5H), 3.43-3.33 (m, 3H), 3.30-3.20 (m, 4H), 2.07-1.85 (m, 4H), 1.59-1.42 (m, 2H), 1.40-1.28 (m, 2H).

Example 4: 4-(((1r,4r)-4-(2-hydroxypropan-2-yl)cyclohexyl)amino)-6-(1H-imidazol-1-yl)-1-methyl-1,5-naphthyridin-2(1H)-one

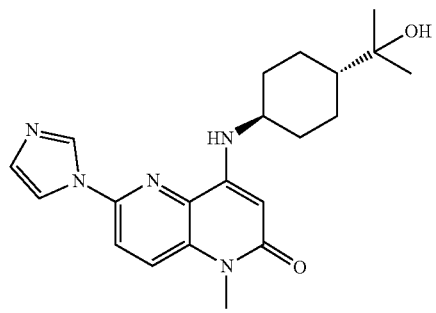

Step 1: 4-(((1r,4r)-4-(2-hydroxypropan-2-yl)cyclohexyl)amino)-6-(1H-imidazol-1-yl)-1-methyl-1,5-naphthyridin-2(1H)-one Under an atmosphere of nitrogen, a solution of 4-chloro-6-(1H-imidazol-1-yl)-1-methyl-1,5-naphthyridin-2(1H)-one (601 mg, 2.31 mmol, 1.0 eq), 2-((1r,4r)-4-aminocyclohexyl)propan-2-ol (544 mg, 3.46 mmol, 1.50 eq), Pd(OAc)$_2$ (51.8 mg, 0.23 mmol, 0.10 eq), BINAP (144 mg, 0.23 mmol, 0.10 eq), and t-BuONa (443 mg, 4.61 mmol, 2.0 eq) in toluene (5 mL) was stirred for 3 h at 75° C. After completion, the reaction was cooled to room temperature and concentrated under vacuum. The crude product was purified by reverse phase chromatography eluting with H$_2$O/ACN (1/1) to afford the title compound (125.2 mg, 14% yield) as a light yellow solid. LCMS: [M+H]$^+$ 382.20.
$^1$H NMR (400 MHz, DMSO-d6) δ 8.89 (s, 1H), 8.25 (s, 1H), 8.06 (dd, J=9.2, 13.2 Hz, 2H), 7.15 (s, 1H), 6.72 (d, J=8.4 Hz, 1H), 5.66 (s, 1H), 4.09 (s, 1H), 3.53 (s, 3H), 3.33-3.26 (m, 1H), 2.10-1.99 (m, 2H), 1.90-1.80 (m, 2H), 1.50-1.38 (m, 2H), 1.32-1.12 (m, 3H), 1.10-1.06 (s, 6H).

Example 5: 4-(((1r,4r)-4-(2-hydroxypropan-2-yl)cyclohexyl)amino)-6-(1H-imidazol-1-yl)-1-methyl-1,7-naphthyridin-2(1H)-one

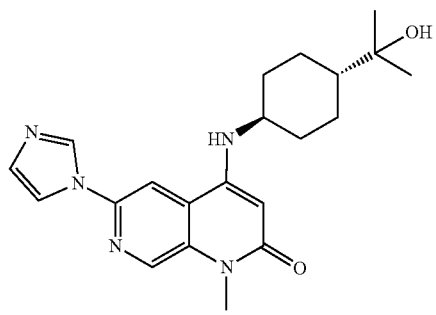 [SMILES: Cn1c(=O)cc(N[C@H]2CC[C@H](C(C)(C)O)CC2)c2cc(-n3ccnc3)ncc21]

Step 1: 5-acetamido-2-chloroisonicotinic acid

A solution of 5-amino-2-chloroisonicotinic acid (10 g, 57.9 mmol, 1 eq), acetic anhydride (11.8 g, 116 mmol, 2.0 eq), and TEA (11.7 g, 116 mmol, 2.0 eq) in THF (30 mL) was stirred for 6 h at RT. The reaction was quenched with water (30 mL) and the pH value of the solution was adjusted to 3 with HCl (2 M). The solids were collected by filtration to afford the title compound (11 g, 88%) as a white solid. LCMS: [M+H]+ 215.00.

Step 2: methyl 2-chloro-5-(N-methylacetamido)isonicotinate

To a solution of 5-acetamido-2-chloroisonicotinic acid (28.0 g, 130 mmol, 1.0 eq) in DMF (250 mL) was added NaH (6.26 g, 261 mmol, 2.0 eq) slowly at 0° C. and the mixture was stirred for 1 h at 0° C. Then MeI (55.56 g, 391 mmol, 3.0 eq) was added to the reaction and the mixture was stirred for another 5 h at RT. The reaction was quenched with water (100 mL) and extracted with EtOAc (3×300 mL). The organic layers were washed with brine (2×300 mL), dried over $Na_2SO_4$, filtered, and concentrated. The crude product was purified by silica gel chromatography eluting with EtOAc/PE (1:1) to afford title compound (27 g 85%) as a yellow solid. LCMS: [M+H]+ 243.10.

Step 3: 6-chloro-1-methyl-1,7-naphthyridine-2,4(1H,3H)-dione

To a solution of methyl 2-chloro-5-(N-methylacetamido)isonicotinate (26.0 g, 107 mmol, 1.0 eq) in THF (30 mL) was added LiHMDS (26.9 g, 161 mmol, 1.5 eq) slowly at 0° C. and the mixture was stirred for 2 h at RT. After completion, the reaction was quenched with water (100 mL) and pH value of the solution was adjusted to 3 with HCl (2 M). The solids were collected by filtration to afford the title compound (19 g, 84%) as a yellow solid. LCMS: [M+H]+ 211.10.

Step 4: 6-(1H-imidazol-1-yl)-1-methyl-1,7-naphthyridine-2,4(1H,3H)-dione

A solution of 6-chloro-1-methyl-1,7-naphthyridine-2,4(1H,3H)-dione (18.0 g, 85.5 mmol, 1.0 eq), 1H-imidazole (46.6 g, 684 mmol, 8.0 eq), $K_2CO_3$ (23.6 g, 171 mmol, 2.0 eq), and CuI (16.3 g, 85.5 mmol, 1.0 eq) in DMSO (200 mL) was stirred at 120° C. for 24 h. After completion, the reaction was concentrated and purified by silica gel chromatography eluting with DCM/MeOH (65/35) to afford the title compound (10 g, 48%) as a yellow solid. LCMS: [M+H]+ 243.05.

Step 5: 4-chloro-6-(1H-imidazol-1-yl)-1-methyl-1,7-naphthyridin-2(1H)-one

A solution of 6-(1H-imidazol-1-yl)-1-methyl-1,7-naphthyridine-2,4(1H,3H)-dione (9.00 g, 37.2 mmol, 1.0 eq) in phosphoryl trichloride (50 mL) was stirred for 2 h at 90° C. After completion, the reaction was concentrated to remove most of phosphoryl trichloride and the residue dissolved in water (100 mL) at 0° C. The pH value of the solution was adjusted to 6 with saturated aqueous $NaHCO_3$. The solids were collected by filtration. The solids were washed with ACN (2×30 mL) and oven dried to afford the title compound (3.1 g, 32%) as a brown solid. LCMS: [M+H]+ 261.05. 1H NMR (300 MHz, DMSO-$d_6$) δ 8.81 (s, 1H), 8.50 (s, 1H), 7.95 (d, J=2.2 Hz, 2H), 7.19 (s, 1H), 7.04 (s, 1H), 3.59 (s, 3H).

Step 6: 4-(((1r,4r)-4-(2-hydroxypropan-2-yl)cyclohexyl)amino)-6-(1H-imidazol-1-yl)-1-methyl-1,7-naphthyridin-2(1H)-one Under an atmosphere of nitrogen, a solution of 4-chloro-6-(1H-imidazol-1-yl)-1-methyl-1,7-naphthyridin-2(1H)-one (398 mg, 1.53 mmol, 1.0 eq), 2-((1r,4r)-4-aminocyclohexyl)propan-2-ol (360 mg, 2.29 mmol, 1.5 eq), $Pd(OAc)_2$ (34.3 mg, 0.15 mmol, 0.10 eq), BINAP (95.1 mg, 0.15 mmol, 0.10 eq), and t-BuONa (293 mg, 3.05 mmol, 2.0 eq) in toluene (3 mL) was stirred for 3 h at 75° C. After completion, the mixture was concentrated under vacuum and purified by silica gel chromatography eluting with DCM/MeOH (95/5). The crude product was concentrated and further purified by reverse phase chromatography eluting with $H_2O$/ACN (1/1) to afford the title compound (93.1 mg, 24%) as a white solid. LCMS: [M+H]+ 382.25. 1H NMR (400 MHz, DMSO-$d_6$) δ 8.72 (s, 1H), 8.50 (d, J=1.1 Hz, 1H), 8.32 (s, 1H), 7.95 (t, J=1.4 Hz, 1H), 7.18 (t, J=1.2 Hz, 1H), 6.71 (d, J=7.5 Hz, 1H), 5.68 (s, 1H), 4.11 (s, 1H), 3.59 (s, 3H), 2.15-2.06 (m, 2H), 1.88-1.81 (m, 2H), 1.33-1.21 (m, 6H), 1.07 (s, 6H).

Example 6: 6-(1H-imidazol-1-yl)-4-(((1r,4r)-4-(2-methoxyethoxy)cyclohexyl)amino)-1-methyl-1,7-naphthyridin-2(1H)-one

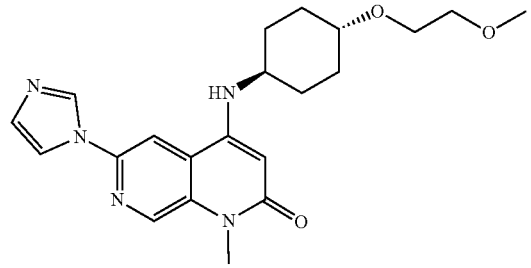 [SMILES: COCCO[C@H]1CC[C@H](Nc2cc(=O)n(C)c3cnc(-n4ccnc4)cc23)CC1]

Step 1: 6-(1H-imidazol-1-yl)-4-(((1r,4r)-4-(2-methoxyethoxy)cyclohexyl)amino)-1-methyl-1,7-naphthyridin-2(1H)-one Under an atmosphere of nitrogen, a solution of 4-chloro-6-(imidazol-1-yl)-1-methyl-1,7-naphthyridin-2-one (156 mg, 0.59 mmol, 1.0 eq), (1r,4r)-4-(2-methoxyethoxy)cyclohexan-1-amine (Int-B1, 156 mg, 0.89 mmol, 1.5 eq), $Pd(OAc)_2$ (13.4 mg, 0.060 mmol, 0.10 eq), BINAP (37.3 mg, 0.060 mmol, 0.10 eq), and t-BuONa (115 mg, 1.19 mmol, 2.0 eq) in toluene (2 mL) was stirred for 2 h at 75° C. The crude product was concentrated under vacuum and purified by reverse phase chromatography eluting with $H_2O$/ACN (65/35). The product was further purified by Prep-HPLC to afford the title compound (44.8 mg, 19%) as a light yellow solid. LCMS: [M+H]+ 398.10. 1H NMR (400 MHz, DMSO-d6) δ 8.72 (s, 1H), 8.48 (s, 1H), 8.29 (s, 1H), 7.93 (d, J=1.4 Hz, 1H), 7.18 (d, J=1.2 Hz, 1H), 6.67 (d, J=7.4 Hz, 1H), 5.72 (s, 1H), 3.60-3.50 (m, 5H), 3.48-3.38 (m, 3H), 3.30-3.23 (m, 4H), 2.08-2.01 (m, 4H), 1.45-1.30 (m, 4H).

Example 7: 2-(1H-imidazol-1-yl)-8-(((1r,4r)-4-(2-methoxyethoxy)cyclohexyl)amino)-5-methylpyrido[3,2-d]pyrimidin-6(5H)-one

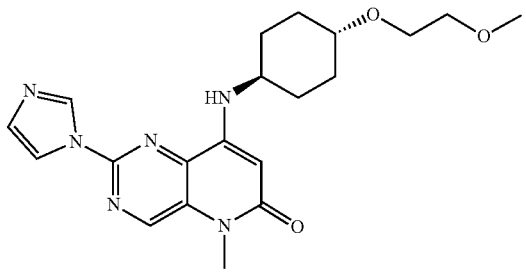 [SMILES: COCCO[C@H]1CC[C@H](Nc2cc(=O)n(C)c3cnc(-n4ccnc4)nc23)CC1]

Step 1: ethyl 2-chloro-5-(methylamino)pyrimidine-4-carboxylate

A solution of ethyl 2-chloro-5-fluoropyrimidine-4-carboxylate (30.0 g, 147 mmol, 1.0 eq), methanamine hydrochloride (9.90 g, 147 mmol, 1.0 eq), and DIEA (56.9 g, 440 mmol, 3.0 eq) in ACN (300 mL) was stirred for 1 h at RT. The reaction was diluted with EtOAc (200 mL) and washed with water (3×200 mL). The organic layer was dried over Na$_2$SO$_4$, filtered, and concentrated under reduced pressure. The crude product was diluted with 200 mL of PE. The solids were collected by filtration and dried to afford title compound (20 g, 63%) as a yellow solid. LCMS: [M+H]$^+$ 216.20.

Step 2: ethyl 2-chloro-5-(N-methylacetamido)pyrimidine-4-carboxylate

A solution of ethyl 2-chloro-5-(methylamino)pyrimidine-4-carboxylate (18.0 g, 83 mmol, 1.0 eq), acetyl chloride (19.7 g, 250 mmol, 3.0 eq), and TEA (16.9 g, 166 mmol, 2.0 eq) in DCM (160 mL) was stirred for 2 days at RT. After completion, the reaction was quenched with water (200 mL) and the mixture was extracted with EtOAc (3×200 mL). The combined organic layers were dried over Na$_2$SO$_4$, filtered, and concentrated under reduced pressure. The crude product was applied onto a silica gel column with EtOAc/PE (1:3) to afford title compound (7.3 g, 34%) as a yellow solid. LCMS: [M+H]$^+$ 257.95.

Step 3: 2-chloro-5-methylpyrido[3,2-d]pyrimidine-6,8(5H,7H)-dione

Under an atmosphere of nitrogen, to a solution of ethyl 2-chloro-5-(N-methylacetamido)pyrimidine-4-carboxylate (7.2 g, 28 mmol, 1.0 eq) in anhydrous THF (60 mL) at 0° C. was added LiHMDS (5.61 g, 33.5 mmol, 1.2 eq) slowly and the mixture was stirred for 1 h at RT. After completion, the reaction was concentrated under vacuum to remove THF then taken up in 30 mL of water. The pH value of the solution was adjusted to 5 with HCl (2 M) and then the solids were collected by filtration to afford title compound (4.2 g, 71%) as a purple solid. LCMS: [M+H]$^+$ 212.00.

Step 4: 2-(1H-imidazol-1-yl)-5-methylpyrido[3,2d]-pyrimidine-6,8(5H,7H)-dione

A solution of 2-chloro-5-methylpyrido[3,2-d]pyrimidine-6,8(5H,7H)-dione (4.00 g, 18.9 mmol, 1.0 eq), imidazole (10.3 g, 151 mmol, 8.0 eq), K$_2$CO$_3$ (5.22 g, 37.8 mmol, 2.0 eq), CuI (3.60 g, 18.9 mmol, 1.0 eq), and L-proline (0.05 g, 0.47 mmol, 0.02 eq) in NMP (40 mL) was stirred for 5 h at 130° C. After completion, the reaction was diluted with 300 mL of MeOH, the solids were filtered out and the filtrate was concentrated under vacuum to remove MeOH. The crude product was purified by silica gel chromatography eluting with DCM/MeOH (4:1) to afford title compound (3.3 g 72%) as a yellow solid. LCMS: [M+H]$^+$ 244.05.

Step 5: 8-chloro-2-(1H-imidazol-1-yl)-5-methylpyrido[3,2-d]pyrimidin-6(5H)-one

A solution of 2-(1H-imidazol-1-yl)-5-methylpyrido[3,2-d]pyrimidine-6,8(5H,7H)-dione (3.10 g, 12.8 mmol, 1.0 equiv) in phosphoryl trichloride (20 mL) was stirred for 1 h at 90° C. After completion, the reaction was concentrated under vacuum then diluted with 100 mL of DCM. The resulting solution was quenched with ice water. The pH value of the solution was adjusted to 8 with saturated aqueous Na$_2$CO$_3$ and extracted with DCM (3×200 mL). The combined organic layers were dried over Na$_2$SO$_4$, filtered and concentrated to afford the title compound (2.3 g, 69%) as a brown solid. LCMS: [M+H]$^+$ 262.05.

Step 6: 2-(1H-imidazol-1-yl)-8-(((1r,4r)-4-(2-methoxyethoxy)cyclohexyl)amino)-5-methylpyrido[3,2-d]pyrimidin-6(5H)-one Under an atmosphere of nitrogen, a solution of 8-chloro-2-(1H-imidazol-1-yl)-5-methylpyrido[3,2-d]pyrimidin-6(5H)-one (1000 mg, 3.82 mmol, 1.0 eq), (1r,4r)-4-(2-methoxyethoxy)cyclohexan-1-amine (Int-B1, 1324 mg, 7.64 mmol, 2.0 eq), Pd(OAc)$_2$ (85.8 mg, 0.38 mmol, 0.10 eq), BINAP (238 mg, 0.38 mmol, 0.10 eq), and Cs2CO3 (2490 mg, 7.64 mmol, 2.0 eq) in toluene (8 mL) was stirred for 3 h at 75° C. After completion, the resulting mixture was concentrated under vacuum. The crude product was purified by C18 reverse phase chromatography eluting with H$_2$O/ACN (3:7). The collected fractions were concentrated under vacuum to remove ACN. The solids were collected by filtration to afford the title compound (567.9 mg, 37%) as a white solid. LCMS: [M+H]$^+$ 399.20. $^1$H NMR (300 MHz, DMSO-d6) δ 9.07 (s, 1H), 8.90 (m, 1H), 8.21 (t, J=1.4 Hz, 1H), 7.14 (t, J=1.2 Hz, 1H), 6.90 (d, J=8.6 Hz, 1H), 5.86 (s, 1H), 3.59-3.49 (m, 5H), 3.47-3.36 (m, 3H), 3.33-3.20 (m, 4H), 2.08-1.89 (m, 4H), 1.55-1.39 (m, 2H), 1.38-1.22 (m, 2H).

Example 8: 8-(((1r,4r)-4-(2-hydroxypropan-2-yl)cyclohexyl)amino)-2-(1H-imidazol-1-yl)-5-methylpyrido[3,2-d]pyrimidin-6(5H)-one

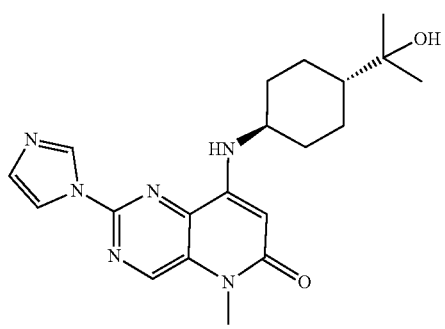 [SMILES: Cn1c(=O)cc(N[C@H]2CC[C@H](C(C)(C)O)CC2)c2nc(-n3ccnc3)ncc21]

Step 1: 8-(((1r,4r)-4-(2-hydroxypropan-2-yl)cyclohexyl)amino)-2-(1H-imidazol-1-yl)-5-methylpyrido[3,2-d]pyrimidin-6(5H)-one Under an atmosphere of nitrogen, a solution of 8-chloro-2-(1H-imidazol-1-yl)-5-methylpyrido[3,2-d]pyrimidin-6(5H)-one (900 mg, 3.44 mmol, 1.0 eq), 2-((1r,4r)-4-aminocyclohexyl)propan-2-ol (1082 mg, 6.88 mmol, 2.0 eq), Pd(OAc)$_2$ (77.2 mg, 0.34 mmol, 0.10 eq), BINAP (214 mg, 0.34 mmol, 0.10 eq), and Cs$_2$CO$_3$ (2241 mg, 6.88 mmol, 2.0 eq) in toluene (7 mL) was stirred at 75° C. for 3 h. After completion, the reaction was concentrated under vacuum. The crude product was purified by C18 reverse phase chromatography eluting with H$_2$O/ACN (32:68). The collected fractions were concentrated under vacuum to remove ACN. The solids were collected by filtration to afford the title compound (682 mg, 52%) as a white solid. LCMS: [M+H]$^+$ 383.25. $^1$H NMR (400 MHz, DMSO-d6) δ 9.07 (s, 1H), 8.92 (t, J=1.1 Hz, 1H), 8.23 (t, J=1.4 Hz, 1H), 7.15 (t, J=1.3 Hz, 1H), 6.93 (d, J=8.5 Hz, 1H), 5.82 (s, 1H), 4.09 (s, 1H), 3.55 (s, 3H), 3.40-3.33 (m, 1H), 2.05-1.98 (m, 2H), 1.89-1.79 (m, 2H), 1.51-1.38 (m, 2H), 1.30-1.12 (m, 3H), 1.06 (s, 6H).

Example 9: 2-(1H-imidazol-1-yl)-5-methyl-8-((4-(trifluoromethyl)phenyl)amino)pyrido[3,2-c]pyrimidin-6(5H)-one

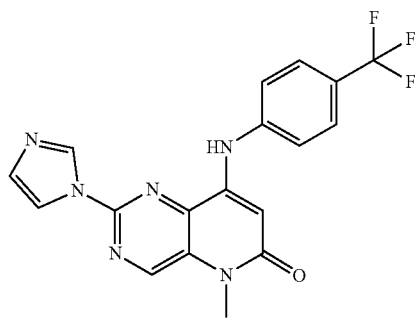 [SMILES: Cn1c(=O)cc(Nc2ccc(C(F)(F)F)cc2)c2nc(-n3ccnc3)ncc21]

Step 1: 2-(1H-imidazol-1-yl)-5-methyl-8-((4-(trifluoromethyl)phenyl)amino)pyrido[3,2-d]pyrimidin-6(5H)-one Under an atmosphere of nitrogen, a solution of 8-chloro-2-(1H-imidazol-1-yl)-5-methylpyrido[3,2-d]pyrimidin-6(5H)-one (150 mg, 0.57 mmol, 1.0 eq), 4-(trifluoromethyl)aniline (185 mg, 1.15 mmol, 2.0 equiv), Pd(OAc)$_2$ (12.9 mg, 0.057 mmol, 0.10 eq), BINAP (35.7 mg, 0.057 mmol, 0.10 eq), and Cs$_2$CO$_3$ (373 mg, 1.15 mmol, 2.0 eq) in toluene (3 mL) was stirred at 80° C. for 4 h. The reaction was concentrated under vacuum. The residue was purified by C18 reverse phase chromatography eluting with H$_2$O/ACN (57:43). The collected fractions were combined and the ACN was removed by concentration. The solids were collected by filtration to afford the title compound (48.4 mg, 22%) as a white solid. LCMS: [M+H]$^+$ 387.15. $^1$H NMR (300 MHz, DMSO-d6) δ 9.30 (s, 1H), 9.22 (s, 1H), 9.00 (s, 1H), 8.32 (t, J=1.4 Hz, 1H), 7.84 (d, J=8.6 Hz, 2H), 7.69 (d, J=8.4 Hz, 2H), 7.19 (t, J=1.2 Hz, 1H), 6.43 (s, 1H), 3.63 (s, 3H).

Example 10: 2-(1H-imidazol-1-yl)-5-methyl-8-((6-(2-morpholinoethoxy)pyridin-3-yl)amino)pyrido[3,2-d]pyrimidin-6(5H)-one

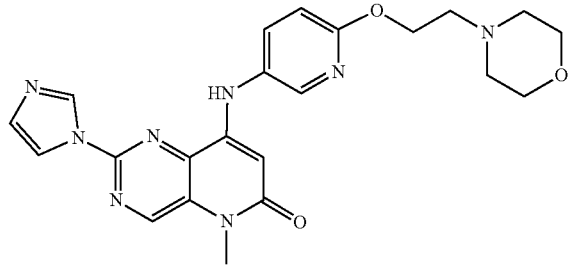 [SMILES: Cn1c(=O)cc(Nc2ccc(OCCN3CCOCC3)nc2)c2nc(-n3ccnc3)ncc21]

Step 1: 4-(2-((5-naropyridin-2-yl)oxy)ethyl)morphohne

A solution of 2-fluoro-5-nitropyridine (724 mg, 5.10 mmol, 1.0 eq), 4-morpholineethanol (1003 mg, 7.64 mmol, 1.5 eq), and t-BuOK (1144 mg, 10.2 mmol, 2.0 eq) in DCM (15 mL) was stirred for 1 h at RT. After completion, the reaction was diluted with 30 mL of DCM and washed with water (3×50 mL.) The organic layers were dried over Na$_2$SO$_4$, filtered, and concentrated. The crude product was purified by silica gel chromatography eluting with EtOAc/PE (3:7) to afford title compound (1.1 g, 85%) as a yellow solid. LCMS: [M+H]$^+$ 254.15.

Step 2: 6-(2-morpholinoethoxy)pyridin-3-amine

Under an atmosphere of hydrogen, a solution of 4-(2-((5-nitropyridin-2-yl)oxy)ethyl)morpholine (600 mg, 2.37 mmol, 1.0 eq) and Pd/C (252 mg, 2.37 mmol, 1.0 eq) in EtOH (6 mL) was stirred for 1 h at RT. After completion, the solids were filtered out and the filtrate was concentrated under vacuum to afford the title compound (502 mg, 93%) as a black oil. LCMS: [M+H]$^+$ 224.15.

Step 3: 2-(1H-imidazol-1-yl)-5-methyl-8-((6-(2-morpholinoethoxy)pyridin-3-yl)amino)pyrido[3,2-d]pyrimidin-6(5H)-one Under an atmosphere of nitrogen, a solution of 8-chloro-2-(1H-imidazol-1-yl)-5-methylpyrido[3,2-d]pyrimidin-6(5H)-one (130 mg, 0.50 mmol, 1.0 eq), 6-(2-morpholinoethoxy)pyridin-3-amine (222 mg, 0.99 mmol, 2.0 eq), Pd(OAc)$_2$ (11.2 mg, 0.050 mmol, 0.10 eq), BINAP (30.9 mg, 0.050 mmol, 0.10 eq), and Cs$_2$CO$_3$ (324 mg, 0.99 mmol, 2.0 eq) in toluene (3 mL) was stirred overnight at 80° C. After completion, the reaction was concentrated under vacuum. The crude product was purified by C18 reverse phase chromatography eluting with H$_2$O/ACN (33:67). The collected fractions were concentrated under vacuum to remove ACN. The solids were collected by filtration to afford the title compound (79.8 mg, 35%) as a yellow solid. LCMS: [M+H]$^+$ 449.20. $^1$H NMR (400 MHz, DMSO-d6) δ 9.16 (s, 1H), 9.08 (s, 1H), 8.94 (d, J=1.2 Hz, 1H), 8.29 (t, J=1.4 Hz, 1H), 8.19 (d, J=2.7 Hz, 1H), 7.78 (dd, J=8.8, 2.8 Hz, 1H), 7.17 (t, J=1.3 Hz, 1H), 6.96 (d, J=8.8 Hz, 1H), 5.80 (s, 1H), 4.41 (t, J=5.8 Hz, 2H), 3.65-3.49 (m, 7H), 2.71 (t, J=5.8 Hz, 2H), 2.55-2.40 (m, 4H).

The following examples in Table 1 were prepared according to the methods described for the previous Examples.

TABLE 1

| Ex. # | Structure and Name | Prepared according to Example # | MS (M + H)+ |
|---|---|---|---|
| 11 | 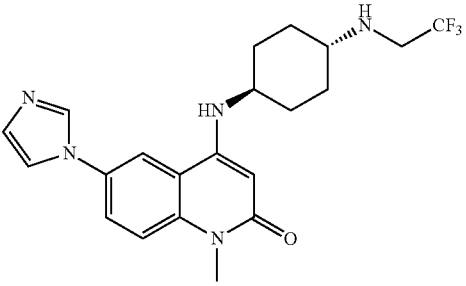<br>6-(1H-imidazol-1-yl)-1-methyl-4-(((1r,4r)-4-((2,2,2-trifluoroethyl)amino)cyclohexyl)amino)quinolin-2(1H)-one | 1 | 420.15 |
| 12 | 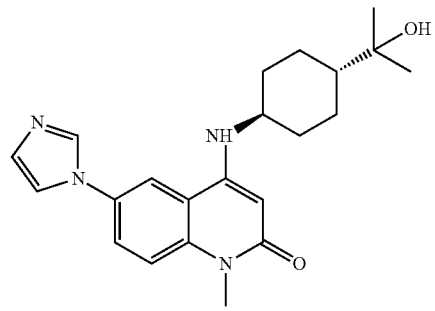<br>4-(((1r,4r)-4-(2-hydroxypropan-2-yl)cyclohexyl)amino)-6-(1H-imidazol-1-yl)-1-methylquinolin-2(1H)-one | 1 | 381.20 |
| 13 | 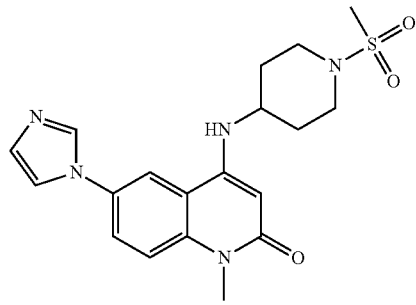<br>6-(1H-imidazol-1-yl)-1-methyl-4-((1-(methylsulfonyl)piperidin-4-yl)amino)quinolin-2(1H)-one | 1 | 402.10 |
| 14 | 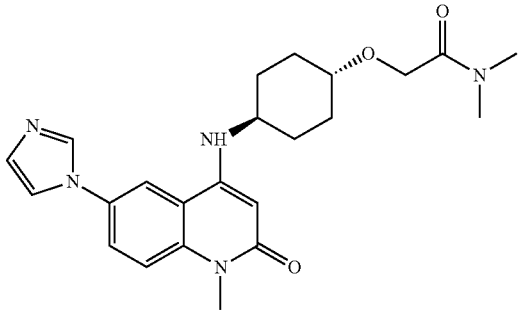<br>2-(((1r,4r)-4-((6-(1H-imidazol-1-yl)-1-methyl-2-oxo-1,2-dihydroquinolin-4-yl)amino)cyclohexyl)oxy)-N,N-dimethylacetamide | 1 | 424.30 |

TABLE 1-continued

| Ex. # | Structure and Name | Prepared according to Example # | MS (M + H)+ |
|---|---|---|---|
| 15 | 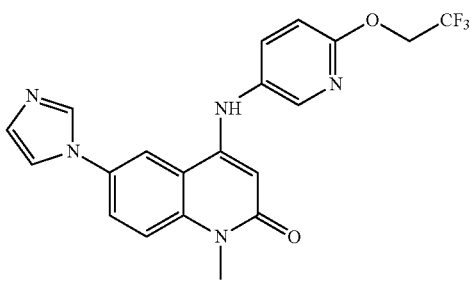<br>6-(1H-imidazol-1-yl)-1-methyl-4-((6-(2,2,2-trifluoroethoxy)pyridin-3-yl)amino)quinolin-2(1H)-one | 1 | 416.15 |
| 16 | 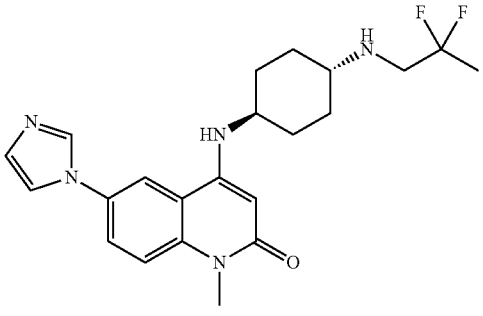<br>4-(((1r,4r)-4-((2,2-difluoropropyl)amino)cyclohexyl)amino)-6-(1H-imidazol-1-yl)-1-methylquinolin-2(1H)-one | 1 | 416.25 |
| 17 | 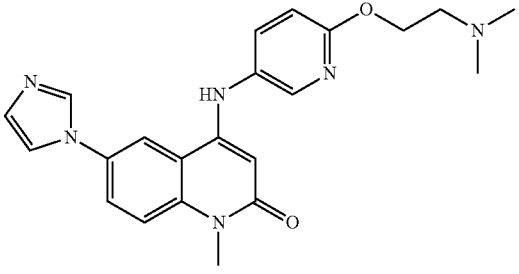<br>4-((6-(2-(dimethylamino)ethoxy)pyridin-3-yl)amino)-6-(1H-imidazol-1-yl)-1-methylquinolin-2(1H)-one | 1 | 405.25 |
| 18 | 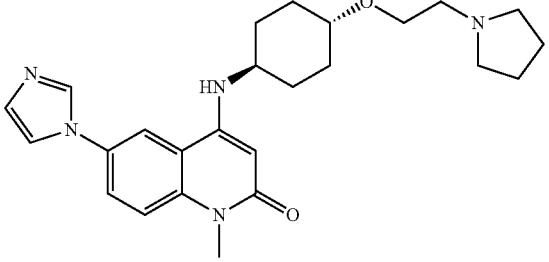<br>6-(1H-imidazol-1-yl)-1-methyl-4-(((1r,4r)-4-(2-(pyrrolidin-1-yl)ethoxy)cyclohexyl)amino)quinolin-2(1H)-one | 1 | 436.30 |

TABLE 1-continued

| Ex. # | Structure and Name | Prepared according to Example # | MS (M + H)+ |
|---|---|---|---|
| 19 | 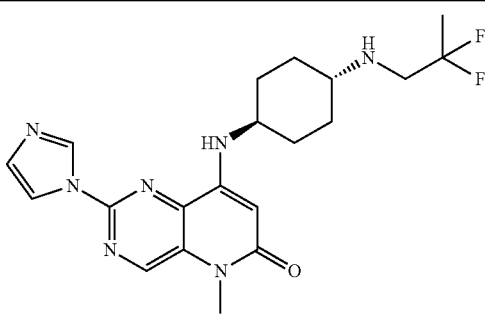<br>8-(((1r,4r)-4-((2,2-difluoropropyl)amino)cyclohexyl)amino)-2-(1H-imidazol-1-yl)-5-methylpyrido[3,2-d]pyrimidin-6(5H)-one | 7 | 418.20 |
| 20 | 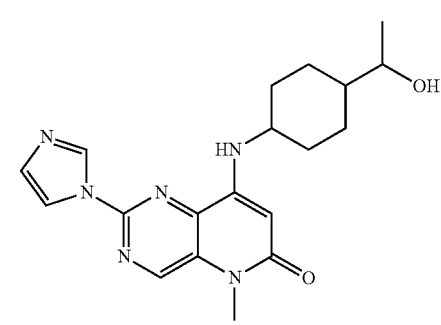<br>8-(1S,4r)-4-((S)-1-hydroxyethyl)cyclohexyl)amino)-2-(1H-imidazol-1-yl)-5-methylpyrido[3,2-d]pyrimidin-6(5H)-one*<br>*Absolute stereochemistry was not determined. | 7 | 369.25 |
| 21 | 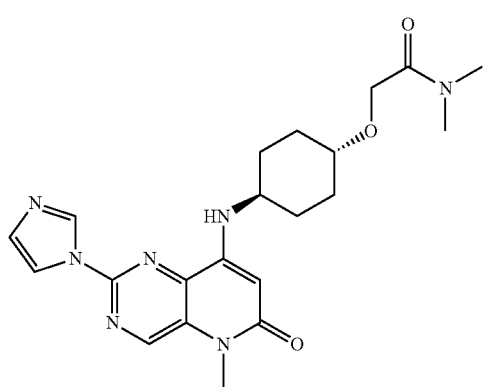<br>2-(((1r,4r)-4-((2-(1H-imidazol-1-yl)-5-methyl-6-oxo-5,6-dihydropyrido[3,2-d]pyrimidin-8-yl)amino)cyclohexyl)oxy)-N,N-dimethylacetamide | 7 | 426.25 |

TABLE 1-continued

| Ex. # | Structure and Name | Prepared according to Example # | MS (M + H)+ |
|---|---|---|---|
| 22 | 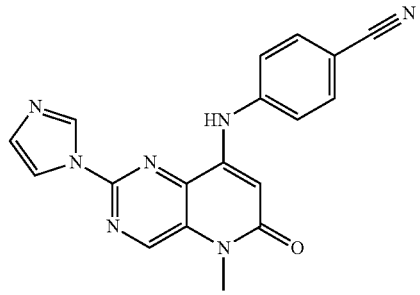<br>4-((2-(1H-imidazol-1-yl)-5-methyl-6-oxo-5,6-dihydropyrido[3,2-d]pyrimidin-8-yl)amino)benzonitrile | 7 | 344.05 |
| 23 | 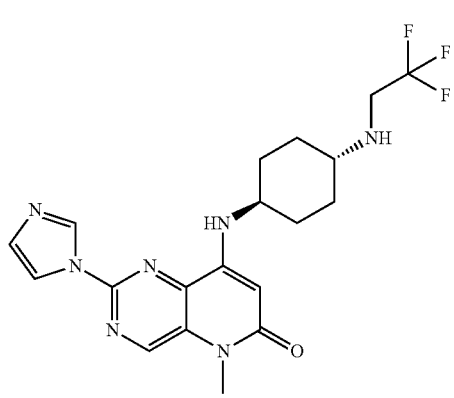<br>2-(1H-imidazol-1-yl)-5-methyl-8-(((1r,4r)-4-((2,2,2-trifluoroethyl)amino)cyclohexyl)amino)pyrido[3,2-d]pyrimidin-6(5H)-one | 7 | 422.15 |
| 24 | 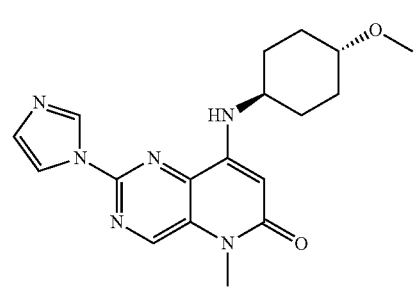<br>2-(1H-imidazol-1-yl)-8-(((1r,4r)-4-methoxycyclohexyl)amino)-5-methylpyrido[3,2-d]pyrimidin-6(5H)-one | 7 | 355.20 |
| 25 | 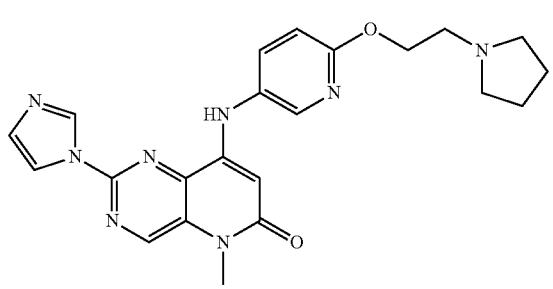<br>2-(1H-imidazol-1-yl)-5-methyl-8-((6-(2-(pyrrolidin-1-yl)ethoxy)pyridin-3-yl)amino)pyrido[3,2-d]pyrimidin-6(5H)-one | 7 | 433.25 |

TABLE 1-continued

| Ex. # | Structure and Name | Prepared according to Example # | MS (M + H)+ |
|---|---|---|---|
| 26 | 8-((4,4-difluorocyclohexyl)amino)-2-(1H-imidazol-1-yl)-5-methylpyrido[3,2-d]pyrimidin-6(5H)-one | 7 | 361.15 |
| 27 | 8-(((1r,4r)-4-(1-hydroxycyclopropyl)cyclohexyl)amino)-2-(1H-imidazol-1-yl)-5-methylpyrido[3,2-d]pyrimidin-6(5H)-one | 7 | 381.15 |

Example 28: 8-(((1r,4r)-4-(2-methoxyethoxy)cyclohexyl)amino)-5-methyl-2-(thiazol-5-yl)pyrido[3,2-d]pyrimidin-6(5H)-one

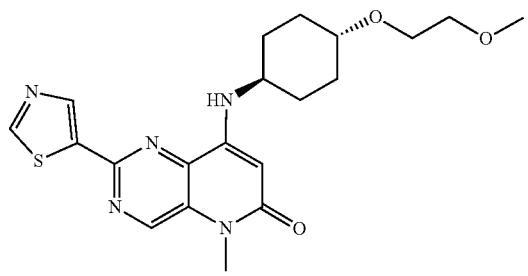 [SMILES: COCCO[C@H]1CC[C@H](Nc2cc(=O)n(C)c3cnc(-c4cncs4)nc23)CC1]

Step 1: ethyl 5-fluoro-2-(thiazol-5-yl)pyrimidine-4-carboxylate

Under an atmosphere of nitrogen, a solution of ethyl 2-chloro-5-fluoropyrimidine-4-carboxylate (4.0 g, 19.5 mmol, 1.0 eq), 5-(tributylstannyl)thiazole (7.7 g, 20.5 mmol, 1.05 eq), Pd(dppf)Cl₂ (1.4 g, 1.9 mmol, 0.1 eq) in DMF (40 mL) was stirred for 2 h at 80° C. After concentration the crude product was purified by reverse phase column eluting with H₂O/ACN (7/3) to afford the title compound (2.7 g, 53%) as a brown solid. LCMS: [M+H]⁺ 254.10.

Step 2: 5-methyl-2-(thiazol-5-yl)pyrido[3,2-d]pyrimidine-6,8(5H,7H)-dione

Under the atmosphere of nitrogen, LiHMDS in THF (7.9 mL, 7.9 mmol, 2.0 eq, 1M) was added slowly to a solution of N-methylacetamide (577 mg, 7.9 mmol, 2.0 eq) in THF (6 mL) at 0° C. The solution was stirred for 1 h at RT. Then to the above mixture was added a solution of ethyl 5-fluoro-2-(thiazol-5-yl)pyrimidine-4-carboxylate (1.0 g, 3.9 mmol, 1.0 eq) in THF (5.0 mL) and was stirred for 1.5 h at RT. The reaction was quenched with water (15 mL). The pH value of the solution was adjusted to 5 with aqueous HCl (1.5 M). The solids were collected by filtration and dried in the oven to afford the title compound (361 mg, 30%) as a brown solid. LCMS: [M+H]⁺ 260.15.

Step 3: 8-chloro-5-methyl-2-(thiazol-5-yl)pyrido[3,2-d]pyrimidin-6(5H)-one

A solution of 5-methyl-2-(thiazol-5-yl)pyrido[3,2-d]pyrimidine-6,8(5H,7H)-dione (400 mg, 1.5 mmol, 1.0 eq) in phosphoryl trichloride (7 mL) was stirred for 2 h at 90° C. The resulting mixture was concentrated to remove most of phosphoryl trichloride. The crude product was dissolved in 50 mL of DCM. The pH value of the solution was adjusted to 8 with saturated aqueous Na₂CO₃. The resulting mixture was concentrated to remove DCM. The solids were collected by filtration and dried in the oven to afford the title compound (266 mg, 62%) as a brown solid. LCMS: [M+H]⁺ 279.25.

Step 4: 8-(((1r,4r)-4-(2-methoxyethoxy)cyclohexyl)amino)-5-methyl-2-(thiazol-5-yl)pyrido[3,2-d]pyrimidin-6(5H)-one Under the atmosphere of nitrogen, a solution of 8-chloro-5-methyl-2-(thiazol-5-yl)pyrido[3,2-d]pyrimidin-6(5H)-one (100 mg, 0.36 mmol, 1.0 eq, (1r,4r)-4-(2-methoxyethoxy)cyclohexan-1-amine (Int-B1, 93.2 mg, 0.54 mmol, 1.5 eq), Pd(OAc)$_2$ (8.06 mg, 0.036 mmol, 0.1 eq), BINAP (22.3 mg, 0.036 mmol, 0.1 eq), and Cs2CO$_3$ (234 mg, 0.72 mmol, 2.0 eq) in toluene (6 mL) was stirred for 2 h at 80° C. The resulting solution was concentrated under vacuum. The crude product was dissolved in 3 mL of DMF and purified by reverse phase column eluting with H$_2$O/ACN (43/57) to afford the title compound (75 mg, 50%) as a light brown solid. LCMS: [M+H]$^+$ 416.20;
$^1$H NMR (400 MHz, DMSO-d$_6$) δ 9.21 (s, 1H), 9.07 (s, 1H), 8.96 (s, 1H), 6.75 (d, J=8.4 Hz, 1H), 5.86 (s, 1H), 3.62-3.50 (m, 5H), 3.48-3.42 (m, 3H), 3.30-3.25 (m, 4H), 2.07-1.96 (m, 4H), 1.60-1.46 (m, 2H), 1.45-1.31 (m, 2H).

Example A

CD38 Enzyme Assay

The CD38 enzyme assay was performed as described previously (Becherer, J D, et al. J. Med. Chem. 2015, 58, 7021-7056). Briefly, 200 nL of a dose response titration of each test compound dissolved in 100% DMSO was spotted in clear polystyrene 384-well plate (Thermo #264704) using a Mosquito (TTP Labtech). A 10 μL solution of 2 nM CD38 (BPS Biosciences #71227) suspended in 100 mM HEPES ((4-(2-hydroxyethyl)-1-piperazineethanesulfonic acid, pH=7.5), 4 mM EDTA (2,2',2'',2'''-(ethane-1,2-diyldinitrilo) tetraacetic acid) and 1 mM CHAPS (3-[(3-cholamidopropy-pdimethylammonio]-1-propanesulfonate) was incubated with test compound at 25° C. for 30 min. The enzyme reaction was initiated by adding 10 μL of 400 μM nicotinamide adenine dinucleotide (NAD$^+$), 1000 μM (E)-2-(2-(pyridin-4-ylmethylene)hydrazineyl)pyridine in buffer containing 5 mM sodium acetate (pH=5.2) and 1 mM CHAPS. The reactions were incubated at 25° C. and the absorbance at 405 nm was measured after 60 minutes on an Envision plate reader (Perkin Elmer).

The compound 4-(((1r,4r)-4-(2-methoxyethoxy)cyclohexyl)amino)-1-methyl-6-(thiazol-5-yl)quinolin-2(1H)-one was synthesized as previously described (Haffner C D, et al. J. Med. Chem. 2015, 58, 3548-3571). Control wells containing a negative control of 1% DMSO vehicle or a positive control of 100 μM 4(((1r,4r)-4-(2-methoxyethoxy)cyclohexyl)amino)-1-methyl-6-(thiazol-5-yl)quinolin-2(1H)-one were used to calculate the % inhibition as described below:

$$\% \text{ inhibition} = 100 \times \frac{CMPD - MIN}{MAX - MIN}$$

where CMPD is the value for the individual compound treated well, MIN is the average of the values of the 4-(((1r,4r)-4-(2-methoxyethoxy)cyclohexyl)amino)-1-methyl-6-(thiazol-5-yl)quinolin-2(1H)-one positive control wells and MAX is the average of the values of the DMSO negative control wells.

The % inhibition values were plotted as a function of compound concentration and the following 4-parameter fit was applied to derive the IC$_{50}$ values:

$$Y = \text{Bottom} + \frac{(\text{Top} - \text{Bottom})}{\left(1 + \frac{X}{IC_{50}}\right)^{\text{Hill Coefficient}}}$$

where top and bottom are normally allowed to float, but may be fixed at 100 or 0 respectively in a 3-parameter fit. The Hill Coefficient is normally allowed to float but may also be fixed at 1 in a 3-parameter fit. Y is the % inhibition and X is the compound concentration.

IC$_{50}$ data for the compounds of the invention according to this assay are provided in Table A-1 below ("+" is <0.01 μM; "++" is ≥0.01 and <0.1 μM; "+++" is ≥0.1 μM and <1 μM; and "++++" is ≥1 μM).

TABLE A-1

| Example No. | Human CD38 IC$_{50}$ (μM) |
| --- | --- |
| 1 | ++ |
| 2 | ++ |
| 3 | ++ |
| 4 | ++ |
| 5 | ++ |
| 6 | ++ |
| 7 | ++ |
| 8 | + |
| 9 | + |
| 10 | ++ |
| 11 | ++ |
| 12 | ++ |
| 13 | ++ |
| 14 | ++ |
| 15 | ++ |
| 16 | ++ |
| 17 | ++ |
| 18 | ++ |
| 19 | + |
| 20 | ++ |
| 21 | ++ |
| 22 | + |
| 23 | + |
| 24 | + |
| 25 | ++ |
| 26 | + |
| 27 | + |
| 28 | ND |

ND = Not determined.

Example B. Treatment with CD38 Inhibitors in Dose Response In Vivo PD Study

Quantification of NAD$^+$

A bioanalytical method for the quantification of NAD$^+$ was developed and utilized for PK/PD studies. The method uses a protein-precipitation (PP) extraction of samples followed by LC/MS/MS analysis and demonstrated a linear assay range from 10 to 10000 ng/mL utilizing a 0.02 mL sample volume. This assay was successfully applied to the analysis of samples such as spleen and liver.

Dexamethasone was used for the internal standard (IS) solution preparation, as shown in the table below:

| Compound ID | MW | FW | Storage Condition |
| --- | --- | --- | --- |
| NAD$^+$ | 663.43 | 663.43 | −20° C. |
| Dexamethasone | 392.40 | 392.40 | −20° C. |

The LC-MS/MS system consisted of Degasser DGU-20A5R, C, Liquid Chromatograph LC-30AD, Communications Bus Module CBM-20A, Auto Sampler SIL-30AC, Rack changer II and an AB Sciex Triple Quads 5500 LC-MS/MS mass spectrometer.

Positive mode electrospray ionization (ESI) was performed on a Turbo V ion source to obtain a protonated ion of $NAD^+$ and Dexamethasone (IS). A multiple reaction monitoring (MRM) method was selected for quantitative analysis. The optimized transitions were 664.038→136.2 and 393.40→373.3 for $NAD^+$ and Dexamethasone, respectively. The instrument parameters were set as follows: ion spray voltage: 5500 V; curtain gas: 40 psi; nebulizer gas: 50 psi; turbo gas: 50 psi; collision gas: 10 psi; temperature: 400° C. The compound dependent parameters are listed in the following table:

| Compound ID | $NAD^+$ | Dexamethasone (IS) |
|---|---|---|
| Transition | 664.038→136.2 | 393.40→373.3 |
| Declustering Potential (DP) | 61 | 59 |
| Collision Energy (CE) | 53 | 17 |
| Collision cell exit Potential (CXP) | 10 | 25 |

$NAD^+$ was prepared in 0.5 N perchloric acid with vortex at 1 mg/mL (free form) as standard stock solution. Calibration standard working solutions were prepared at concentrations of 10, 20, 50, 100, 500, 1000, 2000, 5000 and 10000 ng/mL by serial dilution of the standard stock solution by 50% methanol in water (0.1% Formic acid). Quality control working solutions at concentrations of 20, 50, 500, 4000 and 8000 ng/mL were prepared by serial dilution of the standard stock solution by water. These QC samples were prepared on the day of analysis in the same way as calibration standards. Dexamethasone was prepared in DMSO with vortex at 50 mg/mL (free form) as standard stock solution. Then final concentration of the IS at 50 ng/mL was prepared by dilution of IS stock by methanol (0.1% formic acid).

20 μL of working solutions (10, 20, 50, 100, 500, 1000, 2000, 5000 and 10000 ng/mL) were added to 20 μL of the blank 0.5N perchloric acid to achieve calibration standards of 10~10000 ng/mL (10, 20, 50, 100, 500, 1000, 2000, 5000 and 10000 ng/mL) in a total volume of 40 μL. Five quality control samples at 20 ng/mL, 50 ng/mL, 500 ng/mL, 4000 ng/mL and 8000 ng/mL for 0.5 N perchloric acid were prepared independently of those used for the calibration curves. These QC samples were prepared on the day of analysis in the same way as calibration standards.

The LC-MS/MS system consisted of Degasser DGU-20A5R, C, Liquid Chromatograph LC-30AD, Communications Bus Module CBM-20A, Auto Sampler SIL-30AC, Rack changer II and an AB Sciex Triple Quads 5500 LC/MS/MS mass spectrometer.

Chromatographic separation was performed on a Waters Atlantis T3 3 um 4.6×100 mm at room temperature. The mobile phase was composed of A: 5 mM Ammonium Acetate (0.1% Formic acid); B: Methanol. The flow rate was 0.6 mL/min. The injection volume was 15 μL. The elution gradient is listed in the following table:

| Time (min) | A (%) | B (%) |
|---|---|---|
| 0.10 | 100 | 0.00 |
| 0.20 | 100 | 0.00 |

-continued

| Time (min) | A (%) | B (%) |
|---|---|---|
| 2.60 | 70.0 | 30.0 |
| 3.50 | 10.0 | 90.0 |
| 4.50 | 10.0 | 90.0 |
| 4.51 | 100 | 0.00 |
| 4.8 | 100 | 0.00 |

In Vivo PD Study

C57BL/6 mice were dosed with vehicle, 10, 30, 100, 300 or 1000 mg/kg of the compound of Example 7 in a formulation of 0.5% hydroxypropyl methylcellulose (HPMC)+0.1% Tween 80 adjusted to pH ~3.5 with citric acid buffer. Plasma PK samples were collected at the endpoint. About 500 μL whole blood was collected into a 1.5 mL tube containing 8 μL of 15% dipotassium ethylenediaminetetraacetic acid (EDTA-2K) solution. The sample was centrifuged at 6000 rpm, 4° C. for 5 minutes to isolate about 200 μL of plasma and sent to bioanalysis. Whole spleen, left lobe of liver and whole left kidney without adrenal grand samples were collected at endpoint for $NAD^+$ measurement. Spleen, Liver and Kidney samples were cut down to 100-400 mg/each with the wet weights recorded and placed in a tube containing 0.5 N perchloric acid (1:4 ratio, (mg/μL)) within 30 seconds. The samples were snap frozen in dry ice and stored at −80° C.

Samples were stored in 0.5N perchloric acid immediately after collection and were stored at −80° C. before homogenized due to instability of $NAD^+$ in matrixes at room temperature. Medal bead Lysing matrix was added to each tube along with a 4-fold dilution of the sample with 0.5 N perchloric acid containing a CD38 inhibitor and Dexamethasone. Samples were homogenized on a RETSCH MM40 at 20 m/sec for 60 seconds. The homogenate was diluted with 0.5N perchloric acid for 100 times, then 20 uL diluted samples were mixed with 20 uL 50% methanol in water (0.1% formic acid) and 200 uL methanol (0.1% formic acid) containing internal standard (Dexamethasone) for protein precipitation. Then the samples were vortexed for 30 s. After centrifugation at 4° C., 4000 rpm for 5 min, supernatant was diluted 5 times with 5 mM ammonium formate. 15 μL of the diluted supernatant was injected into the LC/MS/MS system for quantitative analysis.

Figure 1A:
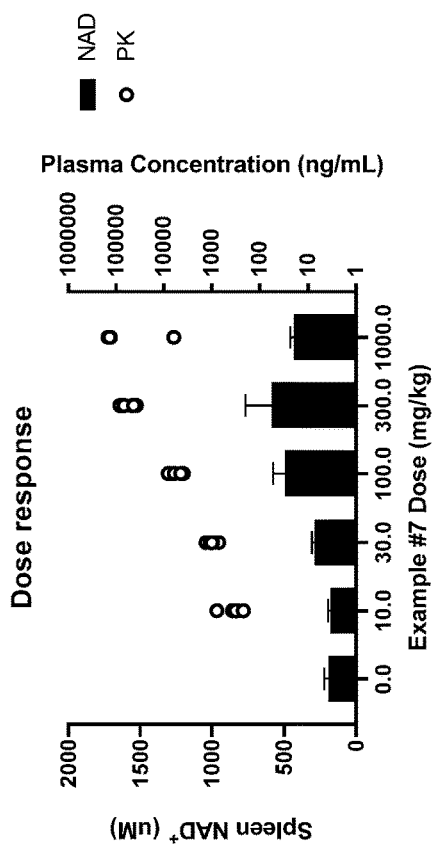
FIG. 1A is a graph of the concentration of NAD+ in the spleen at a single time point after dosing with various amounts of the compound of Example 7.

FIG. 1A is a graph of the concentration of $NAD^+$ in the spleen at a single time point after dosing with various amounts of the compound of Example 7. FIG. 1B is a graph of the concentration of $NAD^+$ in the liver at a single time point after dosing with various amounts of the compound of Example 7.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound, which is 2-(1H-imidazol-1-yl)-8-(((1r,4r)-4-(2-methoxyethoxy)cyclohexyl)amino)-5-methylpyrido[3,2-d]pyrimidin-6(5H)-one, or a pharmaceutically acceptable salt thereof.

2. The compound of claim 1, which is 2-(1H-imidazol-1-yl)-8-(((1r,4r)-4-(2-methoxyethoxy)cyclohexyl)amino)-5-methylpyrido[3,2-d]pyrimidin-6(5H)-one.

3. A pharmaceutical composition comprising a compound of claim 1, or a pharmaceutically acceptable salt thereof, and at least one pharmaceutically acceptable excipient.

4. A compound, which is 8-(((1r,4r)-4-(2-hydroxypropan-2-yl)cyclohexyl)amino)-2-(1H-imidazol-1-yl)-5-methylpyrido[3,2-d]pyrimidin-6(5H)-one, or a pharmaceutically acceptable salt thereof.

5. The compound of claim 4, which is 8(((1r,4r)-4-(2-hydroxypropan-2-yl)cyclohexyl)amino)-2-(1H-imidazol-1-yl)-5-methylpyrido[3,2-d]pyrimidin-6(5H)-one.

6. A pharmaceutical composition comprising a compound of claim 4, or a pharmaceutically acceptable salt thereof, and at least one pharmaceutically acceptable excipient.

7. A compound, which is 8-(((1r,4r)-4-((2,2-difluoropropyl)amino)cyclohexyl)amino)-2-(1H-imidazol-1-yl)-5-methylpyrido[3,2-d]pyrimidin-6(5H)-one, or a pharmaceutically acceptable salt thereof.

8. The compound of claim 7, which is 8-(((1r,4r)-4-((2,2-difluoropropyl)amino)cyclohexyl)amino)-2-(1H-imidazol-1-yl)-5-methylpyrido[3,2-d]pyrimidin-6(5H)-one.

9. A pharmaceutical composition comprising a compound of claim 7, or a pharmaceutically acceptable salt thereof, and at least one pharmaceutically acceptable excipient.

\* \* \* \* \*